(12) United States Patent
Stevenson et al.

(10) Patent No.: US 6,765,779 B2
(45) Date of Patent: Jul. 20, 2004

(54) EMI FEEDTHROUGH FILTER TERMINAL ASSEMBLY FOR HUMAN IMPLANT APPLICATIONS UTILIZING OXIDE RESISTANT BIOSTABLE CONDUCTIVE PADS FOR RELIABLE ELECTRICAL ATTACHMENTS

(75) Inventors: Robert A. Stevenson, Canyon Country, CA (US); Jason Woods, Carson City, NV (US); Christine A. Frysz, Columbia, MD (US); Richard L. Brendel, Carson City, NV (US); Haitong Zeng, Columbia, MD (US)

(73) Assignee: Greatbatch-Sierra, Inc., Carson City, NV (US)

( * ) Notice: Subject to any disclaimer, the term of this patent is extended or adjusted under 35 U.S.C. 154(b) by 0 days.

(21) Appl. No.: 10/377,086

(22) Filed: Feb. 27, 2003

(65) Prior Publication Data

US 2003/0179536 A1 Sep. 25, 2003

Related U.S. Application Data

(60) Provisional application No. 60/360,642, filed on Feb. 28, 2002.

(51) Int. Cl.$^7$ ............................ H01G 4/35; H01G 4/228
(52) U.S. Cl. ......................... 361/302; 361/306.1; 607/5
(58) Field of Search ............................ 361/302, 306.2, 361/306.3, 307, 308.1, 308.2, 308.3, 309–311, 301.2; 333/182–185; 607/5

(56) References Cited

U.S. PATENT DOCUMENTS

| | | |
|---|---|---|
| 2,756,375 A | 7/1956 | Peck |
| 3,235,939 A | 2/1966 | Rodriguez et al. |
| 3,538,464 A | 11/1970 | Walsh |
| 3,920,888 A | 11/1975 | Barr |
| 4,083,022 A | 4/1978 | Nijman |
| 4,144,509 A | 3/1979 | Boutros |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,352,951 A | 10/1982 | Kyle |
| 4,362,792 A | 12/1982 | Bowsky et al. |
| 4,424,551 A | 1/1984 | Stevenson et al. |
| 4,456,786 A | 6/1984 | Kyle |
| 4,737,601 A | 4/1988 | Gartzke |

(List continued on next page.)

OTHER PUBLICATIONS

Dr. Gary Ewell, "A Capacitor's Inductance", Capacitor and Resistor Technology Symposium (CARTS–Europe), Lisbon, Portugal, Oct. 19–22, 1999.

Primary Examiner—Dean A. Reichard
Assistant Examiner—Eric Thomas
(74) Attorney, Agent, or Firm—Kelly Bauersfeld Lowry & Kelley, LLP

(57) ABSTRACT

An EMI feedthrough filter terminal assembly includes a feedthrough filter capacitor having first and second sets of electrode plates, a passageway having a first termination surface conductively coupling the first set of electrode plates, and a second termination surface exteriorly coupling the second set of electrode plates. A conductive ferrule disposed adjacent to the capacitor includes a conductive pad of an oxide resistant biostable material on a surface thereof conductively coupled to the second termination surface. A conductive terminal pin extends through the passageway in conductive relation with the first set of electrode plates, and through the ferrule in non-conductive relation. An insulator is fixed to the ferrule for conductively isolating the terminal pin from the ferrule. A hermetic seal is disposed between the insulator and the ferrule. A second conductive pad may be conductively attached to the terminal pin and to the first termination surface independently of the lead wire.

69 Claims, 22 Drawing Sheets

U.S. PATENT DOCUMENTS

| | | |
|---|---|---|
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,539,611 A | 7/1996 | Hegner et al. |
| 5,670,063 A | 9/1997 | Hegner et al. |
| 5,751,539 A | 5/1998 | Stevenson et al. |
| 5,825,608 A | 10/1998 | Duva et al. |
| 5,867,361 A | 2/1999 | Wolf et al. |
| 5,870,272 A | 2/1999 | Seifried et al. |
| 5,905,627 A | 5/1999 | Brendel et al. |
| 5,959,829 A | 9/1999 | Stevenson et al. |
| 5,973,906 A | 10/1999 | Stevenson et al. |
| 6,008,980 A | 12/1999 | Stevenson et al. |
| 6,031,710 A | 2/2000 | Wolf et al. |
| 6,414,835 B1 | 7/2002 | Wolf et al. |
| 2002/0166618 A1 | 11/2002 | Wolf et al. |

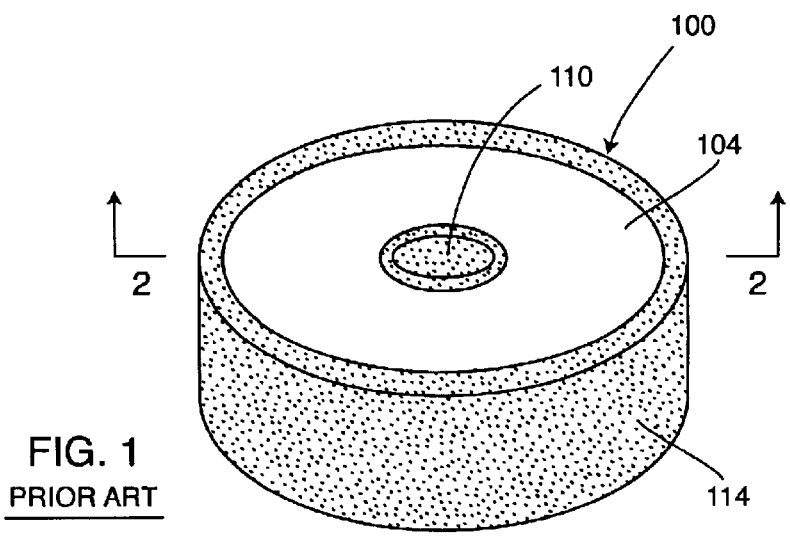
FIG. 1
PRIOR ART
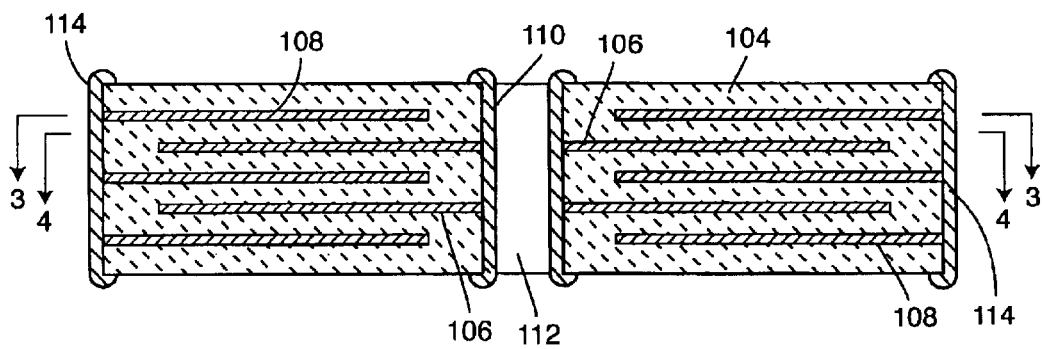
FIG. 2
PRIOR ART
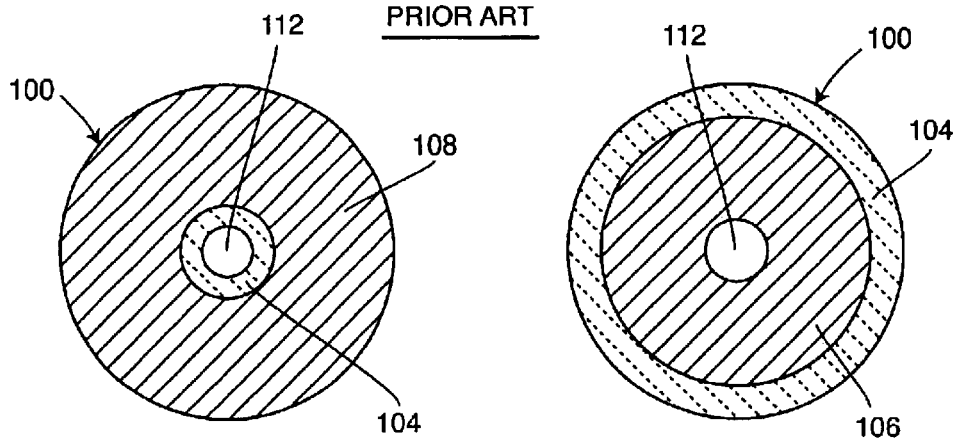
FIG. 3
PRIOR ART
FIG. 4
PRIOR ART C = Capacitance
$R_d$ = R dielectric loss
$R_o$ = R ohmic loss
$R_s$ = R skin effect
IR = Insulation Resistance
ESL = Equivalent Series Inductance
FSR = Equivalent Series Resistance
DF = Dissipation Factor

THERMOPLASTIC POLYIMIDE SUPPORTED TAPE ADHESIVE

| ABLELOC (R) 5500 MECHANICAL PROPERTIES | TEST METHOD |
|---|---|
| 90° Peel Strength - 250 mil (6.3 mm) width<br>Alloy 42 substrate @ 25°C: 5.0 lb$_r$ (2.3 kg$_r$) peak<br>@ 230°C: 1.4 lb$_r$ (0.64 kg$_r$) peak<br><br>PI Coated Si Substrate @ 25°C: 5.5 lb$_r$ (2.5 kg$_r$) peak<br>@ 230°C: 1.2 lb$_r$ (0.55 kg$_r$) peak | MT-8 |
| Flatwise Tensile Strength - 250 mil² (6.3 mm²)<br>Alloy 42 substrate @ 25°C: 3300 psi (93 kg)<br>@ 230°C: 450 psi (13 kg) | MT-1 |

(1) TH exposure - 16 hours, 85°C/85% RH

FIG. 25

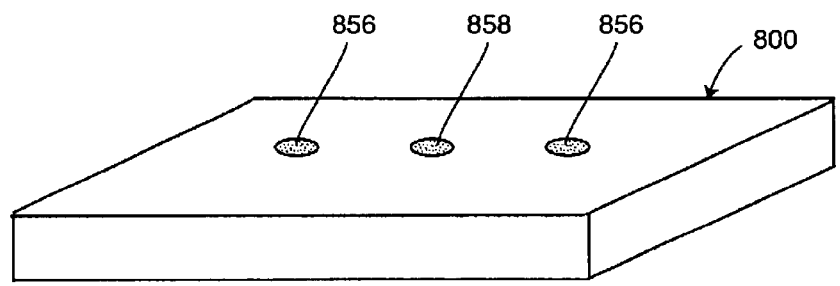
FIG. 31
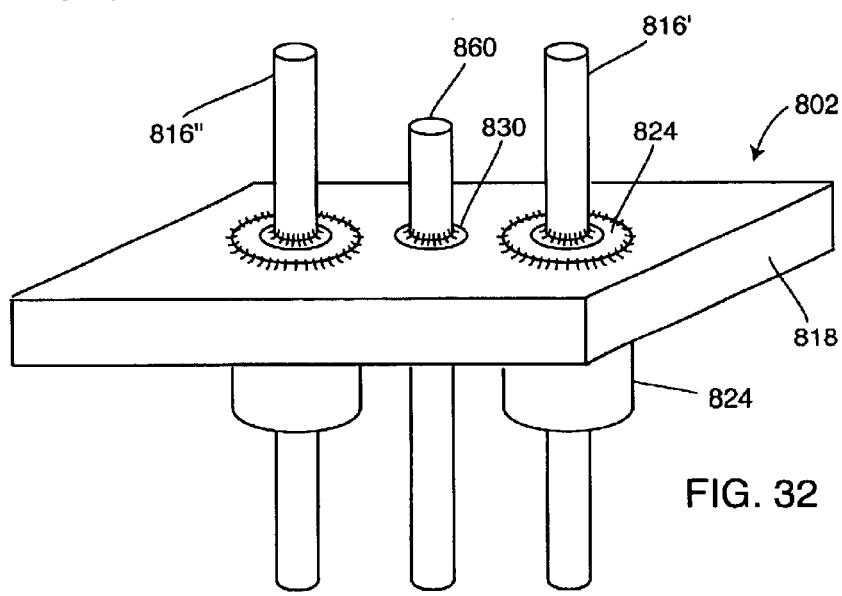
FIG. 32
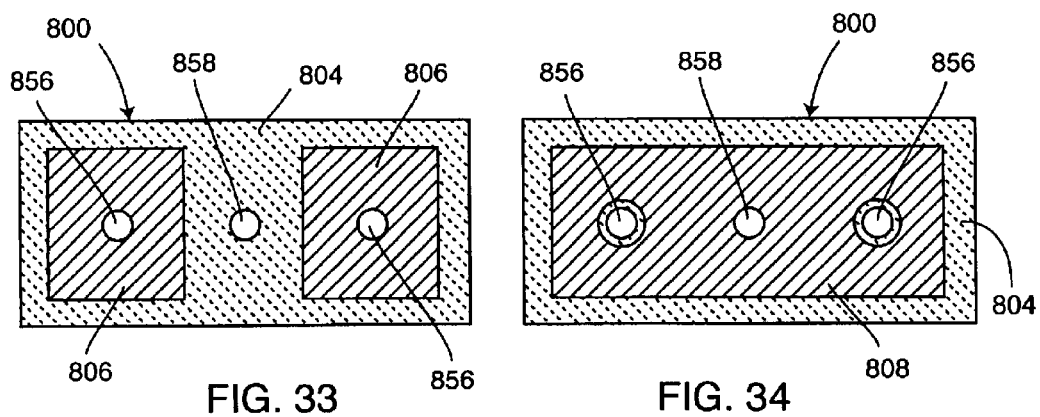
FIG. 33
FIG. 34

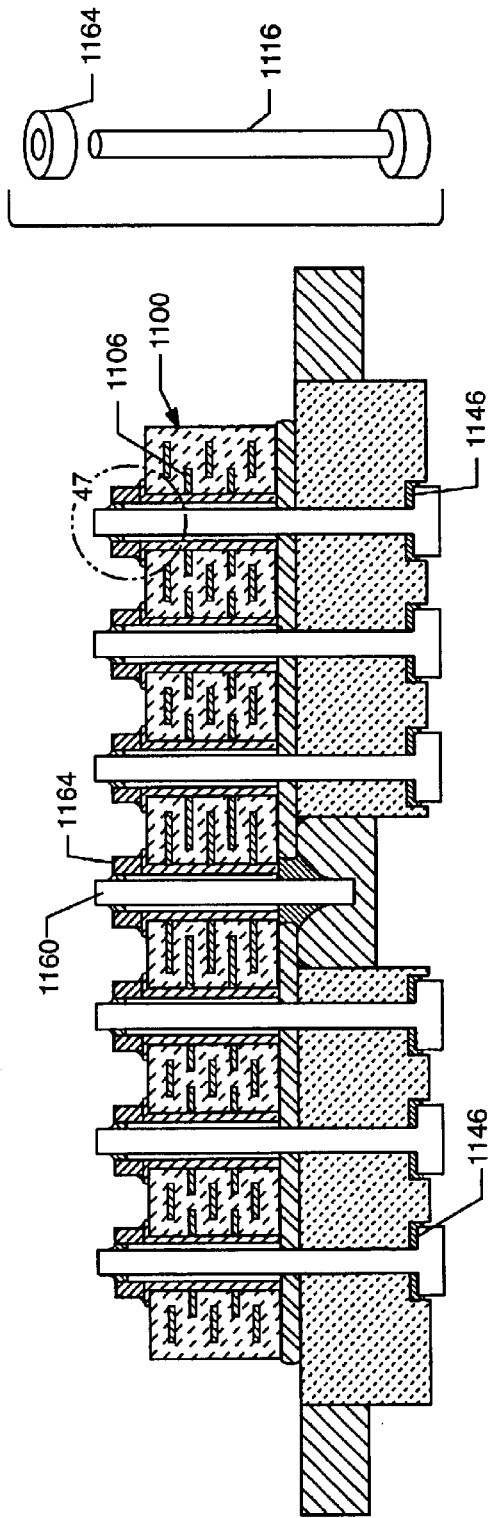

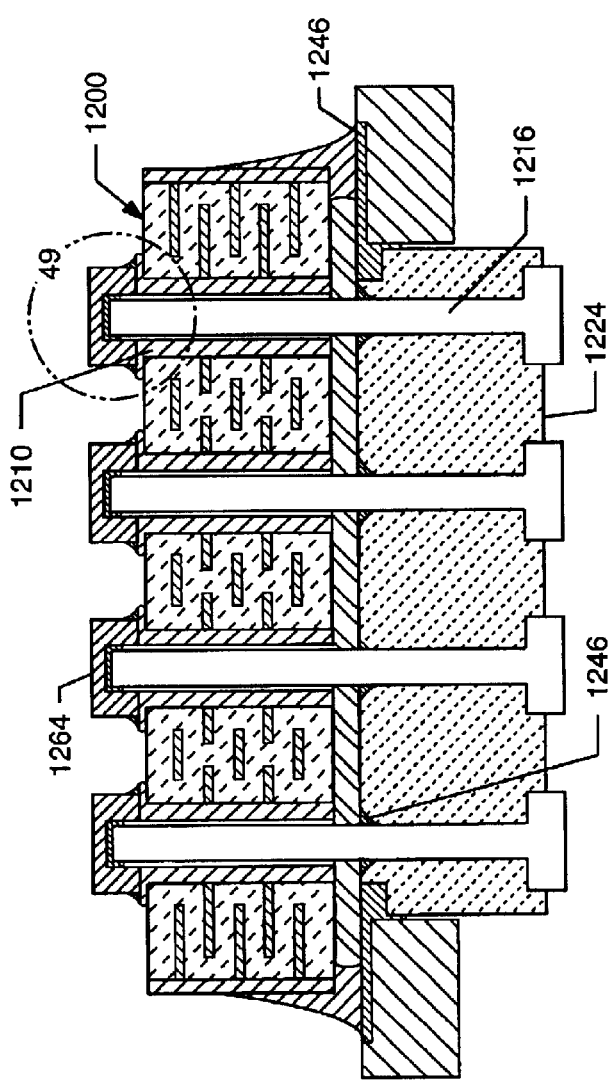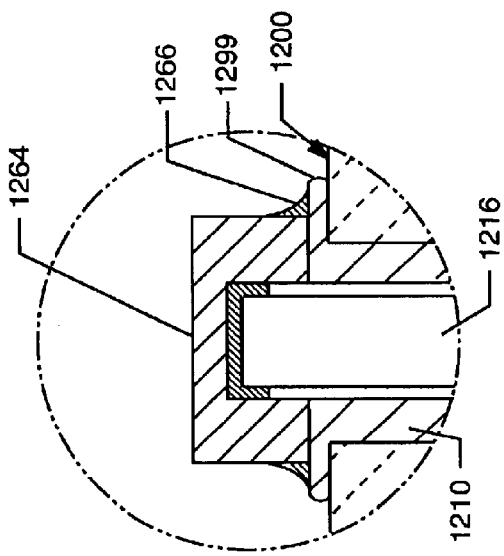
FIG. 48
FIG. 49

EMI FEEDTHROUGH FILTER TERMINAL ASSEMBLY FOR HUMAN IMPLANT APPLICATIONS UTILIZING OXIDE RESISTANT BIOSTABLE CONDUCTIVE PADS FOR RELIABLE ELECTRICAL ATTACHMENTS

RELATED APPLICATION

This application claims priority from Provisional Patent Application Serial No. 60/360,642, filed Feb. 28, 2002.

BACKGROUND OF THE INVENTION

This invention relates generally to feedthrough capacitor terminal pin subassemblies and related methods of construction, particularly of the type used in implantable medical devices such as cardiac pacemakers and the like, to decouple and shield undesirable electromagnetic interference (EMI) signals from the device. More specifically, this invention relates to a method of providing a conductive coating on the flanges of human implantable hermetic seals for reliable EMI filter attachment, and a method of electrical connection of the feedthrough capacitor to the feedthrough lead wires at the hermetic gold braze. This invention is particularly designed for use in cardiac pacemakers (bradycardia devices), cardioverter defibrillators (tachycardia), neuro-stimulators, internal drug pumps, cochlear implants and other medical implant applications. This invention is also applicable to a wide range of other EMI filter applications, such as military or space electronic modules, where it is desirable to preclude the entry of EMI into a hermetically sealed housing containing sensitive electronic circuitry.

Feedthrough terminal pin assemblies are generally well known in the art for connecting electrical signals through the housing or case of an electronic instrument. For example, in implantable medical devices such as cardiac pacemakers, defibrillators or the like, the terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure provides a hermetic seal to prevent entry of body fluids into the housing of the medical device. However, the feedthrough terminal pins are typically connected to one or more lead wires which effectively act as an antenna and thus tend to collect stray EMI signals for transmission into the interior of the medical device. In the prior art devices, the hermetic terminal pin subassembly has been combined in various ways with a ceramic feedthrough filter capacitor to decouple interference signals to the housing of the medical device.

In a typical prior art unipolar construction (as described in U.S. Pat. No. 5,333,095), a round/discoidal (or rectangular) ceramic feedthrough filter capacitor is combined with a hermetic terminal pin assembly to suppress and decouple undesired interference or noise transmission along a terminal pin. FIGS. 1–6 illustrate an exemplary prior art feedthrough filter capacitor 100 and its associated hermetic terminal 102. The feedthrough filter capacitor 100 comprises a unitized dielectric structure or ceramic-based monolith 104 having multiple capacitor-forming conductive electrode plates formed therein. These electrode plates include a plurality of spaced-apart layers of first or "active" electrode plates 106, and a plurality of spaced-apart layers of second or "ground" electrode plates 108 in stacked relation alternating or interleaved with the layers of "active" electrode plates 106. The active electrode plates 106 are conductively coupled to a surface metallization layer 110 lining a bore 112 extending axially through the feedthrough filter capacitor 100. The ground electrode plates 108 include outer perimeter edges which are exposed at the outer periphery of the capacitor 100 where they are electrically connected in parallel by a suitable conductive surface such as a surface metallization layer 114. The outer edges of the active electrode plates 106 terminate in spaced relation with the outer periphery of the capacitor body, whereby the active electrode plates are electrically isolated by the capacitor body 104 from the conductive layer 114 that is coupled to the ground electrode plates 108. Similarly, the ground electrode plates 108 have inner edges which terminate in spaced relation with the terminal pin bore 112, whereby the ground electrode plates are electrically isolated by the capacitor body 104 from a terminal pin 116 and the conductive layer 110 lining the bore 112. The number of active and ground electrode plates 106 and 108, together with the dielectric thickness or spacing therebetween, may vary in accordance with the desired capacitance value and voltage rating of the feedthrough filter capacitor 100.

The feedthrough filter capacitor 100 and terminal pin 116 is assembled to the hermetic terminal 102 as shown in FIGS. 5 and 6. In the exemplary drawings, the hermetic terminal includes a ferrule 118 which comprises a generally ring-shaped structure formed from a suitable biocompatible conductive material, such as titanium or a titanium alloy, and is shaped to define a central aperture 120 and a ring-shaped, radially outwardly opening channel 122 for facilitated assembly with a test fixture (not shown) for hermetic seal testing, and also for facilitated assembly with the housing (also not shown) on an implantable medical device or the like. An insulating structure 124 is positioned within the central aperture 120 to prevent passage of fluid such as patient body fluids, through the feedthrough filter assembly during normal use implanted within the body of a patient. More specifically, the hermetic seal comprises an electrically insulating or dielectric structure 124 such as a gold-brazed alumina or fused glass type or ceramic-based insulator installed within the ferrule central aperture 120. The insulating structure 124 is positioned relative to an adjacent axial side of the feedthrough filter capacitor 100 and cooperates therewith to define a short axial gap 126 therebetween. This axial gap 126 forms a portion of a leak detection vent and facilitates leak detection. The insulating structure 124 thus defines an inboard face presented in a direction axially toward the adjacent capacitor body 104 and an opposite outboard face presented in a direction axially away from the capacitor body. The insulating structure 124 desirably forms a fluid-tight seal about the inner diameter surface of the conductive ferrule 118, and also forms a fluid-tight seal about the terminal pin 116 thereby forming a hermetic seal suitable for human implant. Such fluid impermeable seals are formed by inner and outer braze seals or the like 128 and 130. The insulating structure 124 thus prevents fluid migration or leakage through the ferrule 118 along any of the structural interfaces between components mounted within the ferrule, while electrically isolating the terminal pin 116 from the ferrule 118.

The feedthrough filter capacitor 100 is mechanically and conductively attached to the conductive ferrule 118 by means of peripheral material 132 which conductively couple the outer metallization layer 114 to a surface of the ferrule 118 while maintaining an axial gap 126 between a facing surface of the capacitor body 104, on the one hand, and surfaces of the insulating structure 124 and ferrule 118, on the other. The axial gap 126 must be small to preclude leakage of EMI. The outside diameter connection between the capacitor 100 and the hermetic terminal ferrule 118 is accomplished typically using a high temperature conductive thermal-setting material such as a conductive polyimide. It will also be noted in FIG. 5 that the peripheral support material 132 is preferably discontinuous to reduce mechanical stress and also allow for passage of helium during hermetic seal testing of the complete assembly. In other words, there are substantial gaps between the supports 132 which allow for the passage of helium during a leak detection test.

In operation, the coaxial capacitor 100 permits passage of relatively low frequency electrical signals along the terminal pin 116, while shielding and decoupling/attenuating undesired interference signals of typically high frequency to the conductive housing. Feedthrough capacitors of this general type are available in unipolar (one), bipolar (two), tripolar (three), quadpolar (four), pentapolar (five), hexpolar (six) and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal, such as titanium alloy which is electrically and mechanically coupled to the hermetic terminal pin assembly which in turn is electrically coupled to the feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

It is well known in the art that titanium, has a tendency to form oxides, particularly at high temperature. Titanium oxide (or trioxide) is typical of the oxides that form on the surfaces of titanium. Titanium oxide is very rugged and very stable and in fact is often used as a pigment in paints due to its long-term stability. It is also an insulator or semiconductor.

In the prior art, the attachment between the capacitor outside diameter metallization 114 and the titanium ferrule 118 is accomplished using a thermalsetting conductive adhesive 132, such as a conductive polyimide. Ablestick Corporation manufactures such polyimide compounds. If the oxide layer 134 builds up sufficiently in thickness, this can form an insulative surface which can preclude the proper operation of the feedthrough capacitor 100 as an effective electromagnetic interference filter. It is essential that the capacitor ground electrode plates 108 have a very low resistance and low impedance connection at RF frequencies. This is essential so that it can perform as a proper high frequency bypass element (transmission line) which will short out undesirable electromagnetic interference such as that caused by cellular telephones and other emitters. If the oxide layer 134 is very thin, it creates only a few milliohms of extra resistance. However, recent measurements indicate that a thicker oxide layer can create resistance (measured at 10 MHz) ranging from 750 milliohms to over 30 ohms.

In the past, this oxide layer 134 was very difficult to detect with conventional measuring instruments. Agilent Technologies has recently produced a new piece of equipment known as the E4991A Materials Analyzer. This materials analyzer has the capability to measure equivalent series resistance and other properties of capacitors at very high frequency.

Some background in dielectric theory is required to understand the importance of this. FIG. 7 is the schematic representation for an ideal capacitor C, which does not actually exist. In this regard, all capacitors have varying degrees of undesirable resistance and inductance. This is explained in more detail in "A Capacitor's Inductance," Capacitor and Resistor Technology Symposium (CARTS-Europe), Lisbon, Portugal, Oct. 19–22, 1999, the contents of which are incorporated herein.

FIG. 8 is a simplified equivalent circuit model of the capacitor. For the purposes of these discussions, the IR can be ignored as it is in the millions of ohms and does not significantly contribute to the capacitor equivalent series resistance (ESR). IR also has negligible effect on capacitor high frequency performance. The inductance (ESL) can also be ignored because inductive reactance for monolithic ceramic capacitors is very low at low frequencies. Inductance for a feedthrough capacitor is very low and can be thought of as negligible at high frequencies. Accordingly, the capacitor ESR is the sum of the dielectric loss, the ohmic losses and any losses due to skin effect. However, at low frequency, skin effect is negligible.

Therefore, a good low frequency model for capacitor ESR is as shown in FIG. 9. At low frequency, the capacitor ESR is simply the sum of the capacitor's ohmic and dielectric losses.

FIG. 10 illustrates a normalized curve which shows the capacitor equivalent series resistance (ESR) on the Y axis versus frequency on the X axis. This curve has been highly compressed into a U shape so that all of the important points can be illustrated on one graph. However, one should imagine FIG. 10 stretched out along its X axis by many times to get the true picture. The important point here is the dielectric loss is also known as the dielectric loss tangent. The dielectric material that is used to build the monolithic ceramic capacitor is in itself capable of producing real loss (resistance) which varies with frequency. The dielectric resistance is very high at low frequency and drops to zero at high frequency. This effect can be thought of as oscillations in the crystal structure that produce heat or changes in electronic or electron spin orbits that also produce heat. No matter which dielectric model one uses, this dielectric loss can be very significant at low frequency. In the EMI filter capacitor that's typically used in cardiac pacemakers and implantable defibrillators, a capacitance value of around 4000 picofarads is typical. Typical values of dielectric loss would be around 4000 ohms at 1 kHz, around 6 to 12 ohms at 1 MHz, and only a few milliohms at 10 MHz. This clearly indicates that as one goes up in frequency the dielectric loss tends to disappear.

Since the 1960s it has been a common practice in the capacitor industry to measure capacitance and dissipation factor at 1 kHz. The dissipation factor is usually defined as a percentage, for example, 2.5% maximum. What this means is that the dielectric loss resistance can be no more than 2.5% of the capacitive reactance at a certain frequency (usually 1 kHz). For example, if the capacitive reactance for a particular capacitor was 80,000 ohms at 1 kHz with a 2% dissipation factor this would equate to 1600 ohms of resistance at 1 kHz. FIG. 10 also illustrates that the dielectric loss essentially goes to zero at high frequency. For typical high dielectric constant monolithic ceramic capacitors, anything above 10–20 MHz will be sufficiently high in frequency so that the dielectric loss is no longer a factor in the capacitor ESR measurement. FIG. 10 also has superimposed on it another curve representing conductor ohmic loss which in a monolithic ceramic feedthrough capacitor is typically on the order of 0.25 ohms to 0.75 ohms. It should be pointed out that values of equivalent series resistance presented herein relate to only one illustrative example. In actual fact, the ESR of the capacitor varies with the capacitance value, the number of electrode plates, and the length and width of the electrode plates. Accordingly, a wide range of "normal" ESR readings can be obtained for many types of capacitors. For one particular capacitor a normal ESR reading might be 0.05 ohms and for another design as much as 10 ohms. The important thing is that the ESR reading and the lot population represent oxide free connections that are very homogenous and the readings are stable across the lot population.

It is also possible to detect those parts in a manufacturing lot population that for one reason or another have an abnormally high resistance reading. This can be done at 1 MHz by very tightly controlling the maximum allowable ESR. This is being done in the presence of relatively high dielectric loss. However, by holding a very tight screening limit it is still possible to detect such out of population part. This measurement is, of course, easier to do at 10 MHz, but also quite practical at 1 MHz.

The conductor ohmic losses come from all of the feedthrough capacitor conductor materials and connections. That would include the lead wire or circuit trace itself, the electrical connection between the lead wire and the capacitor metallization, which might be solder or a thermalsetting conductive adhesive, the interface between the capacitor metallization and the internal electrode plates, the connection from the capacitor ground metallization to a ferrule, and the bulk resistance of the electrode plates themselves. Conductor ohmic loss does not vary with frequency until skin effect comes into play. Skin effect is also shown on FIG. 10 and one can see that the resistance starts to climb at the higher frequencies. For physically small MLC chips and feedthrough capacitors, skin effect does not really play a role until one gets to very high frequencies, for example, above 200 MHz.

FIG. 11 is a more detailed illustration of the dielectric loss shown by itself. At very low frequency the dielectric loss in ohms is quite high and as frequency increases, one can see that dielectric loss tends to go to zero. On this scale, the conductor ohmic losses, which are shown as metal loss, can hardly be detected (these are only a few milliohms in this case).

As previously mentioned, titanium oxide (or niobium or tantalum oxides) can vary in resistance from a few milliohms all the way up to 10 or even 30 ohms. A recently discovered problem is that when one makes measurements at 1 kHz it is impossible to see the effects of these oxides because they are hidden by the dielectric loss tangent, which can be as high as 4000 ohms or more by itself. Trying to find a resistance that has increased from 0.25 ohms for a titanium surface that is free of oxide up to 2 ohms is literally impossible in the presence of 4000 ohms of dielectric loss. The reason for this is that the dielectric loss can vary slightly from part to part (typically plus or minus 20 percent). Therefore, when one is making measurements on a manufacturing lot of ceramic EMI feedthrough capacitors for medical implant applications, the part to part variation at 1 kHz can be as much as 100 ohms due to dielectric loss tangent variation alone. Therefore, it becomes quite impossible to detect the presence of this undesirable oxide layer on the titanium surface. However, the recently introduced Agilent equipment is capable of making dielectric equivalent series resistance measurements at 10 MHz and above. This is a high enough frequency to get rid of the dielectric loss so that one can see the ohmic loss by itself (without being hidden under the dielectric loss).

FIG. 12 is a sweep from the Agilent E4991A RF Impedance-Materials Analyzer. Curve 136 illustrates the capacitor equivalent series resistance vs. frequency. The presence of these oxides can reduce EMI filter performance by as much as 20 dB. Stated another way, this could reduce EMI filtering effectiveness by a ratio of 10 to 1 or more. This is highly undesirable in an implantable medical device given the previous documented clinical interactions between cellular telephones and pacemakers. For example, it has been shown that cellular telephone interference can completely inhibit a pacemaker or cause it to go into asynchronous tracking or other undesirable behavior. This can be very dangerous even life threatening for a pacemaker-dependent patient. Further compounding this concern is the recent introduction throughout the marketplace of cellular telephone amplifiers.

One example of this is in the off shore marine boating environment. Until recently maritime communications were primarily limited to the VHF radio. However, many boaters are now relying on cellular telephones for their communication. Accordingly, a number of companies have introduced cellular telephone amplifiers which boost cellular telephone output from 0.6 watts maximum to 3 watts. In addition, high gain marine antennas are being manufactured which can be anywhere from 4 to 8 feet long. These provide an additional 9 dB of gain in the extreme case. Passengers on these boats are being subjected to much higher field intensities than were previously contemplated by the FDA.

Another area where cellular telephone amplifiers are becoming increasingly popular is for wireless Internet connections for lap top computers. It is now possible to buy small black box devices that plug into the wall and also plug into the cellular telephone. These devices then plug into the lap top computer. This boosts the cellular telephone output to 3 watts and also provides a high gain antenna all of which sit on a desk top right in front of the operator. There are also remote credit card scanning devices that operate under similar principles. In short, the public is increasingly being exposed to higher levels of electromagnetic fields.

Accordingly, there is an urgent and present need for EMI filtered terminals for implantable medical devices that will not only maintain their present performance (by not degrading in the presence of oxides) but also increase in their performance. Co-bonded ferrite slabs are being contemplated in order to further increase filter performance in conjunction with the principles outlined here. This will allow future capacitor connections with very low ESR and very low potential for oxidation at attachment points. In addition, the additional ferrite slab will change it from a single element EMI filter to a double EMI filter (L filter). Accordingly, increased performance at cellular phone frequencies offered thereby providing complete immunity to the aforementioned new signal amplifiers. Returning to FIG. 12 one can see from the resistance curve 136 that at the far left hand side of the sweep (1) at 1 MHz, the resistance is approximately 6 ohms. This means that there is a significant, but small amount of dielectric loss tangents still present at 1 MHz (the dielectric loss tangent at 1 kHz is 1800 ohms). However, when one goes up to marker (2), which is at 10 MHz, we're at a point where the dielectric loss tangent has all but disappeared. At this point, we are primarily seeing the true ohmic losses of the device. The device measured in FIG. 12 has no titanium oxide build-up. Accordingly, at marker (2) we have a very low resistance measurement of 234.795 milliohms (0.234 ohms).

FIG. 13 is the same as the sweep in FIG. 12 except this is taken from a part that has a substantial amount of undesirable titanium oxide build-up. Curve 136 illustrates that at marker (2) there is 23.2529 ohms of resistance present. FIG. 13 clearly illustrates that there is enough titanium oxide build-up to create 23.2529 ohms of series resistance at 10 MHz (a normal reading is 0.234 ohms for this particular capacitor). This is highly undesirable because it will preclude the proper operation of an EMI filter at this frequency and frequencies above.

FIGS. 14–19 illustrate a prior art rectangular bipolar feedthrough capacitor (planar array) 200 mounted to the hermetic terminal 202 of a cardiac pacemaker in accordance with U.S. Pat. No. 5,333,095. Functionally equivalent parts shown in this embodiment relative to the structure of FIGS. 1–6 will bear the same reference number, increased by 100.

As illustrated in FIGS. 14–19, in a typical broadband or low pass EMI filter construction, a ceramic feedthrough filter capacitor, 200 is used in a feedthrough assembly to suppress and decouple undesired interference or noise transmission along one or more terminal pins 216, and may comprise a capacitor having two sets of electrode plates 206 and 208 embedded in spaced relation within an insulative dielectric substrate or base 204, formed typically as a ceramic monolithic structure. One set of the electrode plates 206 is electrically connected at an inner diameter cylindrical surface of the capacitor structure 200 to the conductive terminal pins 216 utilized to pass the desired electrical signal or signals (see FIG. 16). The other or second set of electrode plates 208 is coupled at an outer edge surface of the capacitor 200 to a rectangular ferrule 218 of conductive material (see FIG. 18). The number and dielectric thickness spacing of the electrode plate sets varies in accordance with the capacitance value and the voltage rating of the capacitor 200.

In operation, the coaxial capacitor 200 permits passage of relatively low frequency electrical signals along the terminal pins 216, while shielding and decoupling/attenuating undesired interference signals of typically high frequency to the conductive housing. Feedthrough capacitors 200 of this general type are available in unipolar (one), bipolar (two), tripolar (three), quadpolar (four), pentapolar (five), hexpolar (6) and additional lead configurations. Feedthrough capacitors 200 (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the hermetic terminal pin assembly which is in turn electrically coupled to the coaxial feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

FIG. 15 illustrates an unfiltered hermetic terminal 202 typical of that used in medical implant applications. The ferrule 218 is typically made of titanium or other biocompatible material. An alumina insulator 224 or other insulative material such as glass or the like, is used to electrically isolate the leads 216 from the conductive ferrule while at the same time providing a hermetic seal against body fluids. In the case of an alumina insulator, the lead wires or leads 216 are installed into the insulating material 224 typically by gold brazing. A gold braze is also formed between the alumina 224 and the ferrule 218. In some applications, this can also be done with sealing glass so that the gold brazes are not required. The reference numbers 228 and 230, on the one hand, and 228' and 230', on the other (FIG. 19), show gold brazes in two alternate locations that are used to form the hermetic seal between the titanium ferrule 218 and the alumina insulator 224.

FIG. 18 illustrates the capacitor 200 mounted to the hermetic terminal 202 of FIG. 15. The attachment 232 between the capacitor ground metallization 214 and the titanium ferrule 218 is typically done with a conductive thermalsetting polymer, such as conductive polyimide or the like. It is also required that an electrical/mechanical connection be made between the capacitor inside diameter holes 212 and the four lead wires 216. This is shown at 244 and can be accomplished with a thermalsetting conductive adhesive, solder, welding, brazing or the like.

FIG. 19 is a cross-sectional view of the capacitor assembly of FIG. 18, which is typical of prior art capacitors shown in U.S. Pat. No. 5,333,095 and related patents. In FIG. 19, one can see the undesirable oxide layer 234. This oxide layer can actually coat all surfaces of the titanium ferrule (for simplicity, it is only shown on FIG. 19 in the area where the conductive polyimide attachment 232 is made to the capacitor ground termination 214). The thermalsetting conductive material 232 connects between the capacitor ground metallization 214 and the ferrule 218. However, if there is an insulative titanium oxide layer 234 as shown, this can preclude the proper operation of the feedthrough capacitor 200 as previously mentioned.

From the foregoing it is seen that titanium housings, casings and ferrules for hermetic seals are commonly used in the medical implant industry. Pacemakers, implantable defibrillators, cochlear implants and the like, all have ferrules or housings made of titanium. All of the aforementioned devices are also subject to electromagnetic interference (EMI) from emitters that are commonly found in the patient environment. These include cell phones, microwave ovens and the like. There are a number of prior art patents which describe EMI feedthrough filters which make the implantable devices immune to the effects of EMI.

The presence of oxides of titanium can preclude the proper performance of monolithic ceramic EMI feedthrough filters. The titanium oxides that form during manufacturing processes or handling form a resistive layer, which shows up at high frequency. High frequency impedance analyzer plots of resistance vs frequency illustrate that this effect is particularly prominent above 10 MHz. There is a significant need, therefore, for a novel method of providing a conductive coating on the ferrules of human implantable hermetic seals for reliable EMI filter attachment. Further, there is a need for a novel method of electrical connection of feedthrough capacitor lead wire inside diameter termination directly to the gold termination or other similarly capable material of hermetic seals and corresponding lead wire(s). The present invention fulfills these needs and provides other related advantages.

SUMMARY OF THE INVENTION

The present invention resides in an EMI feedthrough filter terminal assembly which utilizes oxide resistant, biostable conductive pads, for example gold or the like, for reliable and stable electrical attachments. Broadly, the EMI feedthrough filter terminal assembly comprises a feedthrough filter capacitor, a conductive ferrule, a conductive terminal pin, and an insulator that is fixed to the ferrule for conductively isolating the terminal pin from the ferrule.

More particularly, the feedthrough filter capacitor includes first and second sets of electrode plates, a passageway therethrough having a first termination surface conductively coupling the first set of electrode plates, and a second termination surface which exteriorly couples the second set of electrode plates. The conductive ferrule is disposed adjacent to the feedthrough filter capacitor and has a noble metal pad on a surface thereof which is conductively coupled to the second termination surface. At least one conductive terminal pin extends through the passageway in conductive relation with the first set of electrode plates. The terminal pin also extends through the ferrule in non-conductive relation. An insulative washer is sometimes disposed between the feedthrough filter capacitor and the insulator.

In illustrated embodiments of the present invention the terminal assembly includes means for hermetically sealing passage of the terminal pin through the ferrule. The ferrule and the insulator comprise a pre-fabricated hermetic terminal pin sub-assembly.

The second termination surface may comprise a plurality of second termination surfaces. In such case, an oxide resistant conductive hermetic seal includes a corresponding plurality of pads of oxide resistant conductive biostable material, conductively coupled to the plurality of second termination surfaces. Conductive connectors extend between the respective sets of second termination surfaces and conductive pads. The conductive pads of oxide resistant biostable material, typically comprise gold bond pads that may be associated with a titanium/molybdenum base. The conductive connectors are typically taken from the group consisting of conductive polyimide or solder.

The first passageway through the feedthrough filter capacitor may comprise a plurality of first passageways each having a distinct first termination surface which is conductively coupled to a distinct first set of electrode plates. In such case, the at least one conductive terminal pin comprises a terminal pin extending through each of the plurality of first passageways.

A second conductive pad of an oxide resistant biostable material may be conductively attached to the lead wire. Means are then provided for conductively coupling the second conductive pad to the first termination surface independently of the lead wire. Such structure utilizes conductive pads of oxide resistant biostable material, for reliable electrical attachments to both the first and second sets of electrode plates.

An insulative washer may be disposed between the feedthrough filter capacitor and the insulator. When the second conductive pad is provided which is conductively attached to the at least one lead wire, the washer includes a gap adjacent to the terminal pin.

Preferably, the EMI feedthrough filter terminal assembly is specifically constructed for medical implant applications including cardiac pacemakers, implantable cardioverter defibrillators, cochlear implants, neuro-stimulators, implantable drug pumps and the like.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a top and side perspective view of a typical unipolar ceramic discoidal feedthrough capacitor;

FIG. 2 is an enlarged sectional view taken generally along the line 2—2 of FIG. 1;

FIG. 3 is a horizontal section taken along the line 3—3 of FIG. 2, illustrating the configuration of the ground electrode plates within the capacitor;

FIG. 4 is a horizontal section taken generally along the line 4—4 of FIG. 2, illustrating the configuration of the active electrode plates within the capacitor;

FIG. 25 is a chart illustrating the mechanical properties of thermoplastic polyimide supported tape adhesive;

FIG. 31 is a perspective view of an internally grounded bipolar rectangular feedthrough capacitor as illustrated and described in U.S. Pat. No. 5,905,627;

FIG. 32 is a perspective view of a hermetic terminal suitable for use with the internally grounded feedthrough capacitor of FIG. 31;

FIG. 33 is a sectional view through the capacitor of FIG. 31, illustrating the active electrode plates;

FIG. 34 is a sectional view similar to FIG. 33, illustrating the configuration of the ground electrode plates;

FIG. 45 is a sectional view similar to FIG. 43, illustrating an internally grounded hex polar capacitor and related hermetic terminal embodying the present invention;

FIG. 46 is an enlarged perspective view of a terminal pin utilized in the structure of FIG. 45;

FIGS. 47A–C are an enlarged fragmented and sectional views of the area indicated by the line 47 in FIG. 45, illustrating three different embodiments of attachment of the lead wire;

FIG. 48 is a sectional view similar to FIGS. 43 and 45, illustrating an externally grounded quadpolar device; and FIG. 49 is an enlarged fragmented view of the area 49 shown on FIG. 48.

DETAILED DESCRIPTION OF THE PREFERRED EMBODIMENTS

Figure 5:
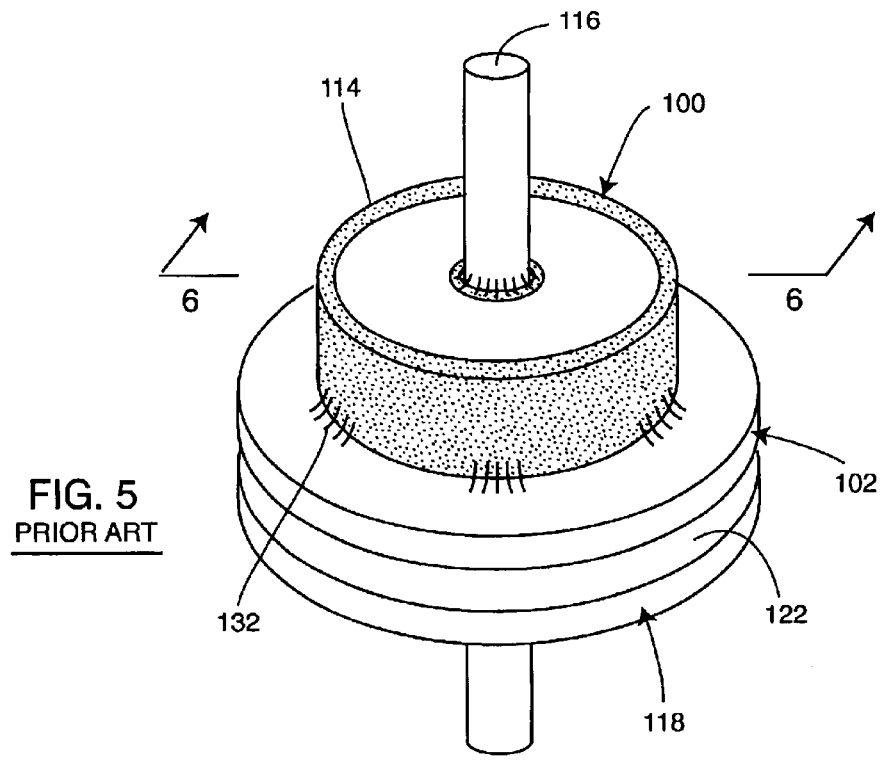
FIG. 5 is a perspective view of the capacitor of FIGS. 1–4, mounted to a typical hermetic terminal.
Figure 6:
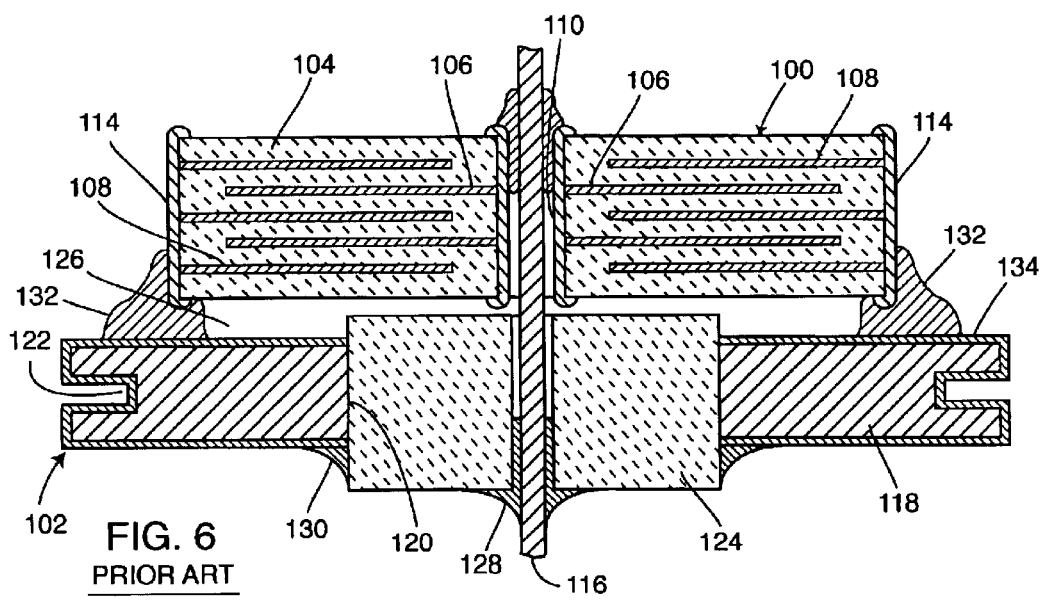
FIG. 6 is an enlarged sectional view taken generally along the line 6—6 of FIG. 5.
Figure 7:
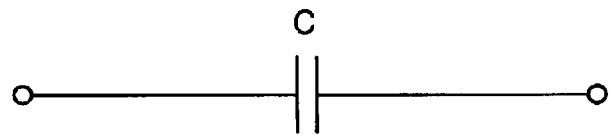
FIG. 7 is a schematic representation of an ideal capacitor.
Figure 8:
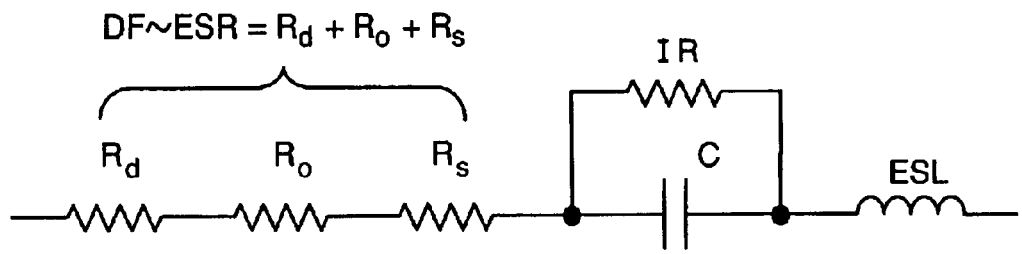
FIG. 8 is a simplified equivalent circuit model for a real capacitor.

Titanium housings, casings and ferrules for hermetic seals are commonly used in the medical implant industry. Pacemakers, implantable defibrillators, cochlear implants and the like, all have ferrules or housings made of titanium or titanium-ceramic composite structures. All of the aforementioned devices are also subject to electromagnetic interference (EMI) from emitters that are commonly found in the patient environment. These include cell phones, microwave ovens and the like. There are a number of prior art patents which describe EMI feedthrough filters which make the implantable devices immune to the effects of EMI.

The inventors have noted that the presence of oxides of titanium can preclude the proper performance of monolithic ceramic EMI feedthrough filters. The titanium oxides that form during manufacturing processes or handling form a resistive layer. High frequency impedance analyzer plots of resistance vs frequency illustrate this effect is particularly prominent above 10 MHz. The novel invention as described herein deposits an oxide resistant conductive coating on the surface of the titanium to provide a resistively stable area to which the ground electrode plates of the feedthrough capacitor can be reliably and consistently attached. Attachments between the capacitor ground electrode plates are typically performed in the prior art by a conductive termination layer which is a part of the feedthrough capacitor, wherein the termination layer connects the ground electrode plates in parallel. The termination material as described in the prior art provides a convenient electrical and solderable connection to the capacitor ground electrode plates. The active electrode plates are similarly terminated at their inside diameter (feedthrough holes).

The primary role of the EMI filter capacitor is to appear as a very low impedance at RF frequencies. The presence of resistance due to a titanium oxide in the capacitor connection undesirably raises its overall impedance. Oxides of titanium are additionally problematic in that they are not stable with time and temperature (they can continue to build-up). These oxides can preclude the proper filtering function of the capacitor. For example, the presence of 23.25 ohm titanium oxide(s) resistance overwhelms the impedance of the feedthrough capacitor, which generally measures less than 600 milliohms at the HF frequency band. This means that the feedthrough capacitor is no longer an effective EMI filter.

The reason that EMI filters are placed at the point of lead ingress in implantable medical devices such as cardiac pacemakers, implantable defibrillators and the like, is to be sure that the implanted electronic device will continue to operate properly in the presence of electromagnetic fields. A notorious example is the microwave oven. It wasn't that many years ago that a number of serious interactions were documented between microwave ovens and cardiac pacemakers and warning signs appeared in stores and other places that were using such devices. The titanium housing that encompasses modern implantable devices largely precludes problems from microwave ovens along with effective EMI filters. Another notable example is the cellular telephone (and other hand held wireless communication devices). Extensive testing by the FDA, by Mount Sinai Medical Center, by Oklahoma University, the Mayo Clinic and other institutions has documented serious interactions between cellular telephones and cardiac pacemakers and implantable defibrillators. In implantable defibrillators, inappropriate therapy delivery has been documented. This means that the defibrillator delivers a painfully high voltage shock where it is not necessary to cardiovert the heart. In this case the implantable defibrillator has confused electromagnetic interference with a chaotic ventricular rhythm. EMI filters that properly decouple these signals provide the degree of patient safety that is required. However, if the filter performance degrades in the presence of the oxides as mentioned, then the patient is clearly at risk. This means that the elimination of these oxides is essential to eliminate a serious public safety concern.

The connection between the capacitor ground termination and the titanium ferrule is typically done using a thermalsetting conductive material such as a conductive polyimide material or the like. The reason for this is that titanium is not solderable. The use of conductive thermalsetting materials to make this connection is well known in the art.

The novel conductive coating of the titanium ferrule of the hermetic seal as described herein is accomplished in one of a variety of ways:

1. Deposition of gold braze material in selected areas of the flange that line up with the capacitor ground electrode terminations. Accordingly, electrical connection between capacitor termination and the gold braze material can still be accomplished as described in the prior art using the conductive polyimide. A novel feature of the invention is that said connection is now achievable with conventional soldering processes.
2. Physical vapor deposition, e.g. sputtering of various materials such as gold or platinum, and various other conductively joinable materials onto the titanium surface.
3. Selected electroplating of gold, platinum, or other materials on the titanium flange for the purposes of facilitating the capacitor ground electrode connection.
4. Plasma arc deposition
5. Ion beam
6. Chemical vapor deposition
7. Laser ablation
8. Or any other deposition method that will achieve the end result described.

It should be apparent to those skilled in the art that the techniques described herein are also applicable to other hermetic seal ferrule materials like niobium, tantalum, and the like. The present invention is also applicable to a variety of other hermetic seal applications as used in oil well logging, aerospace, military and other applications.

A related invention is also shown in the accompanying drawings. This is the unique capability of connecting directly between the lead wire and the gold braze. This is of great advantage for lead materials that form heavy oxide layers, are non-solderable, or both. For biomedical applications, this allows the use of titanium, niobium, tantalum and other lead materials which are much less expensive than the current platinum or platinum-iridium leads.

In the following description, elements of the feedthrough filter capacitor assemblies described herein which are functionally equivalent to one another and to the feedthrough filter capacitor assemblies of FIGS. 1–6 and 14–19 described above, will retain common reference numbers, but increased in increments of 100.

Figure 15:
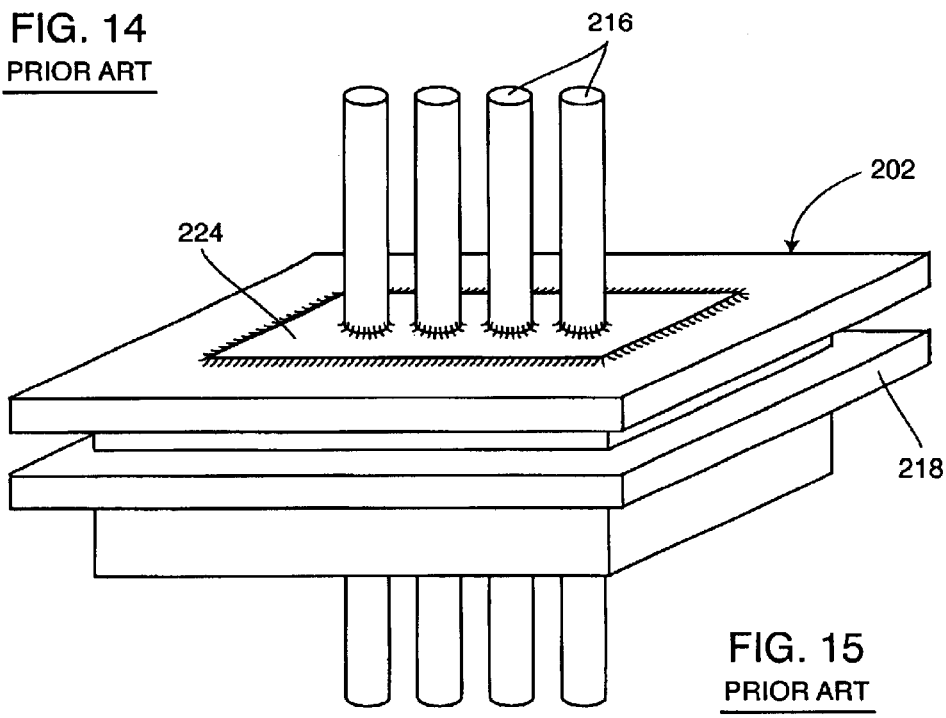
FIG. 15 is a perspective view of a prior art unfiltered hermetic terminal typical of that used in medical applications.
Figure 16:
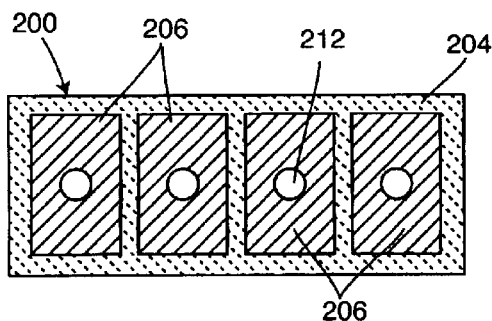
FIG. 16 is a horizontal section taken generally along the line 16—16 of FIG. 14, illustrating the configuration of active electrode plates within the capacitor.
Figure 17:
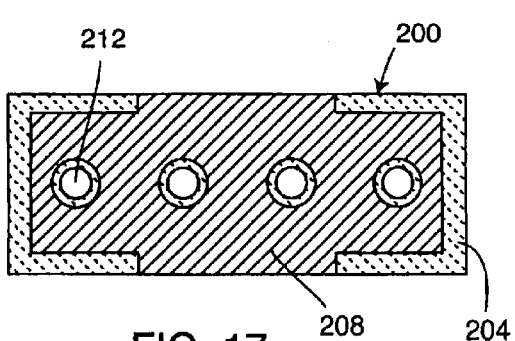
FIG. 17 is a horizontal section taken generally along the lines 17—17 of FIG. 14, illustrating the configuration of a set of ground electrode plates within the capacitor.
Figure 18:
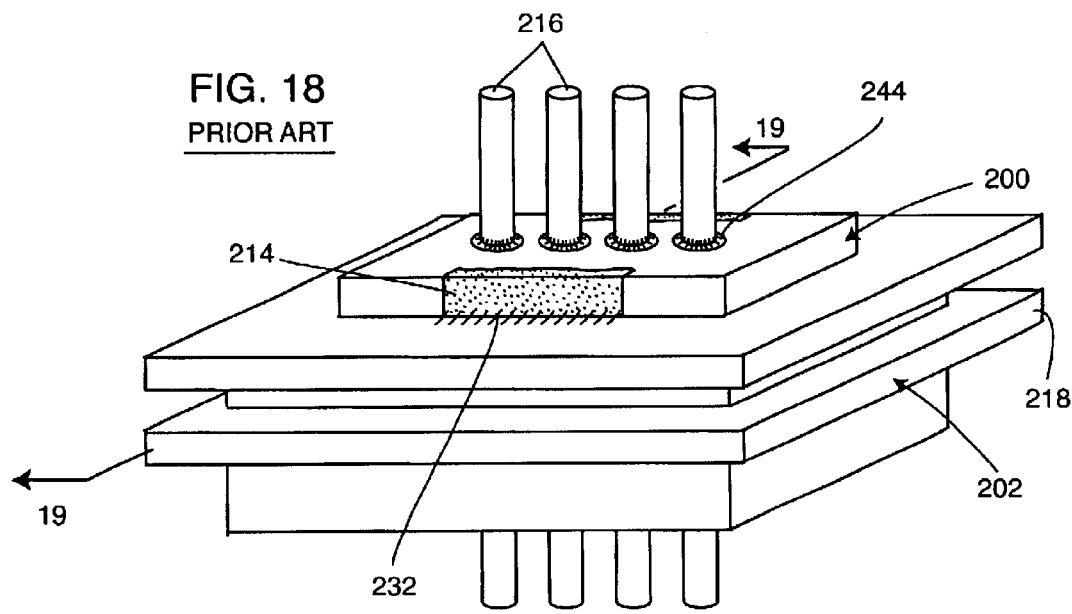
FIG. 18 illustrates the capacitor of FIG. 14 mounted to the hermetic terminal of FIG. 15.
Figure 19:
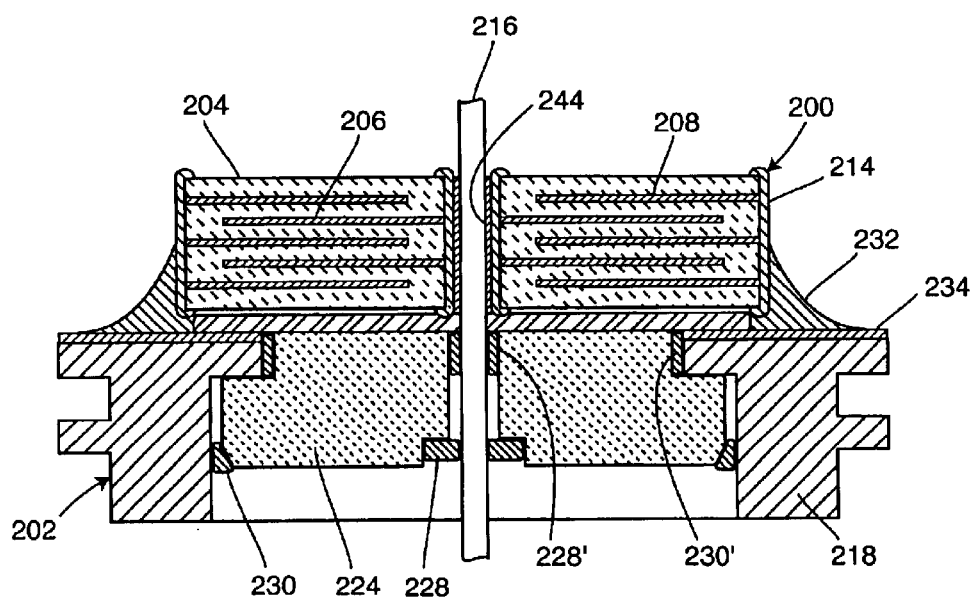
FIG. 19 is an enlarged sectional view taken generally along the line 19—19 of FIG. 18.
Figure 20:
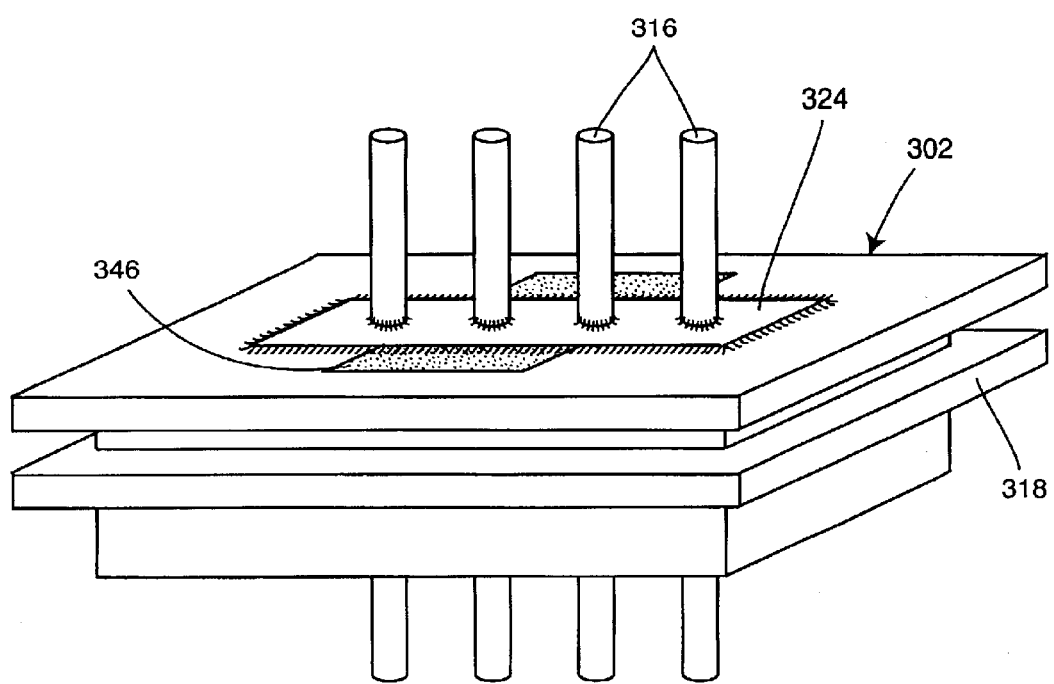
FIG. 20 is a hermetic terminal similar to that illustrated in FIG. 15, but modified in accordance with features of the present invention.

FIG. 20 illustrates a hermetic terminal 302 which is similar to the hermetic terminal 202 of FIG. 15, but which has been modified in accordance with the present invention by extending a gold braze area 346 to create a rectangular pad as shown. The gold braze 346, which runs around the alumina insulator 324, is also run into two pockets that are convenient for capacitor mounting.

Figure 21:
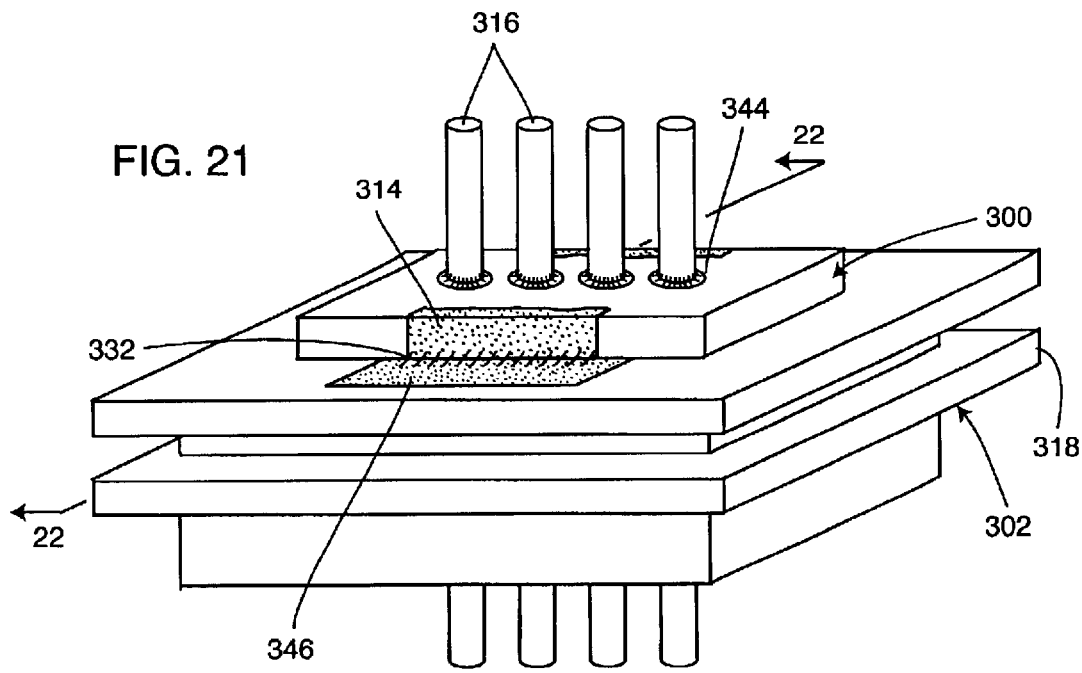
FIG. 21 is a perspective view similar to FIG. 18, illustrating a rectangular feedthrough capacitor mounted to the hermetic terminal of FIG. 20.

FIG. 21 shows a quadpolar feedthrough capacitor 300 (which is identical to the capacitor 200 of FIG. 14) mounted to the hermetic terminal of FIG. 20. As one can see in FIG. 21, the conductive polyimide material 332 now connects between the capacitor metallization 314 and the gold braze area 346. The gold braze forms a metallurgical bond with the titanium and precludes any possibility of an oxide forming. Gold is a noble metal that does not oxidize and remains very stable even at elevated temperatures. The novel construction methodology illustrated in FIG. 21 guarantees that the capacitor ohmic losses will remain very small at all frequencies.

Figure 22:
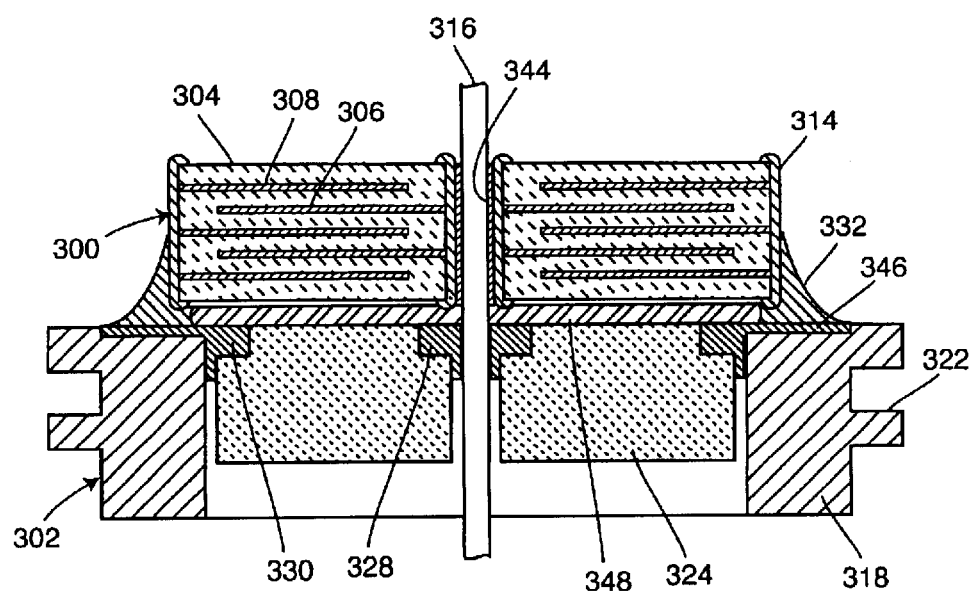
FIG. 22 is an enlarged sectional view taken generally along the line 22—22 of FIG. 21.

FIG. 22 is a cross-section of the capacitor shown in FIG. 21. One can see that the gold braze (or weld) areas 328 and 330 that form the hermetic seal between the alumina insulator 324 and the titanium ferrule 318 are desirably on the feedthrough capacitor side. This makes it easy to manufacture the gold bond pad area 346 for convenient attachment of the conductive thermalsetting material 332. In other words, by having the gold braze hermetic seals on the same side as the gold bond pad area, these can be co-formed in one manufacturing operation in a gold braze vacuum furnace. Further, a unique thermalsetting material 348 is disposed between the capacitor 300 and the underlying hermetic terminal 302.

Another feature of the present invention is that in the prior art only conductive thermalsetting materials could be used to electrically connect the capacitor ground metallization 314 to the ferrule 318. This is because titanium, niobium, tantalum and other biocompatible materials used for human implant ferrules are generally not solderable. With the present invention, it is now possible to replace the thermalsetting conductive adhesive with solder. Solder paste could also be used. This is because solder will properly wet and bond to the gold braze area 346. Solder reflow operations tend to be more cost efficient (more automatable) as compared to dispensing of thermalsetting conductive adhesives. It should also be noted that the gold bond pad area 346 of FIG. 21 could be achieved using other methods. Gold brazing is one method that has already been described. However, sputter coatings of material surfaces such as gold, platinum or other conductive materials could be done. In addition, the gold bond pad area 346 could be done by electroplating of a suitable material that would form an electrical bond to the titanium and preclude oxide formation or by any other deposition method capable of achieving the desired result.

Accordingly, it will be understood that a novel feature of the present invention is the capability of producing a hermetic seal using noble materials such as gold braze while at the same time forming a gold bond pad or landing area to which to connect the capacitor ground metallization. With specific reference to FIG. 22, the hermetic seal 330 forms a hermetic braze connection between the ferrule 302 and the alumina insulator 324. This also, at the same time, forms the gold bond pad 346 for convenient connection of the conductive polyimide 332. The conductive polyimide forms the electrical connection between the capacitor ground electrode plates through the capacitor metallization 314 which connects directly to the conductive polyimide 332 and to gold bond pad 346.

There are a number of advantages in having the hermetic connection 330 be co-formed with gold bond pad 346. First of all there is a very significant manufacturing advantage to having this all done in one operation. A single gold pre-form can be used, which is formed to accommodate the area as shown. In addition, this can all be done in one batch of product put into the vacuum gold brazing furnace at one time. In a typical manufacturing operation of the hermetic terminal, batches of parts are placed into carbon/graphite holding/alignment fixtures called boats, the lead wires and alumina and gold pre-forms along with the ferrules are then all loaded into this special fixture. The operator then places these in a sealed chamber known as a vacuum brazing furnace. Then over a period of time, the temperature is raised sufficiently to re-flow the gold braze material. The gold makes a connection between sputtering, which was formerly placed on the alumina terminal 324 so that good wetting takes place, and a hermetic seal is formed. There is also a good wetting to the titanium such that a hermetic seal is formed there also. This can all be done in one continuous operation wherein the gold only wets to the titanium in the selected areas where the conductive polyimide 332 is to be placed. Accordingly, the structure as shown in 332 in FIG. 22 can all be formed in one manufacturing step with very little added cost. There is also an electrical advantage to doing it this way. By extending the gold bond pad over the greater area to include the hermetic seal portion of the gold braze, there is additional contact area of the gold to the titanium thereby further lowering the contact resistance related to the formation of oxides as previously mentioned herein. It has been demonstrated that the formation of these oxides can reduce the effectiveness of an EMI filter at high frequency. This is because the titanium oxide would increase the capacitor's equivalent series resistance thereby adding an undesirable resistance in series with the bypass capacitor.

Figure 9:
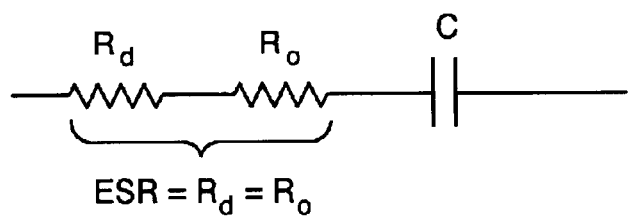
FIG. 9 is a schematic illustrating a low frequency model for capacitor ESR.
Figure 10:
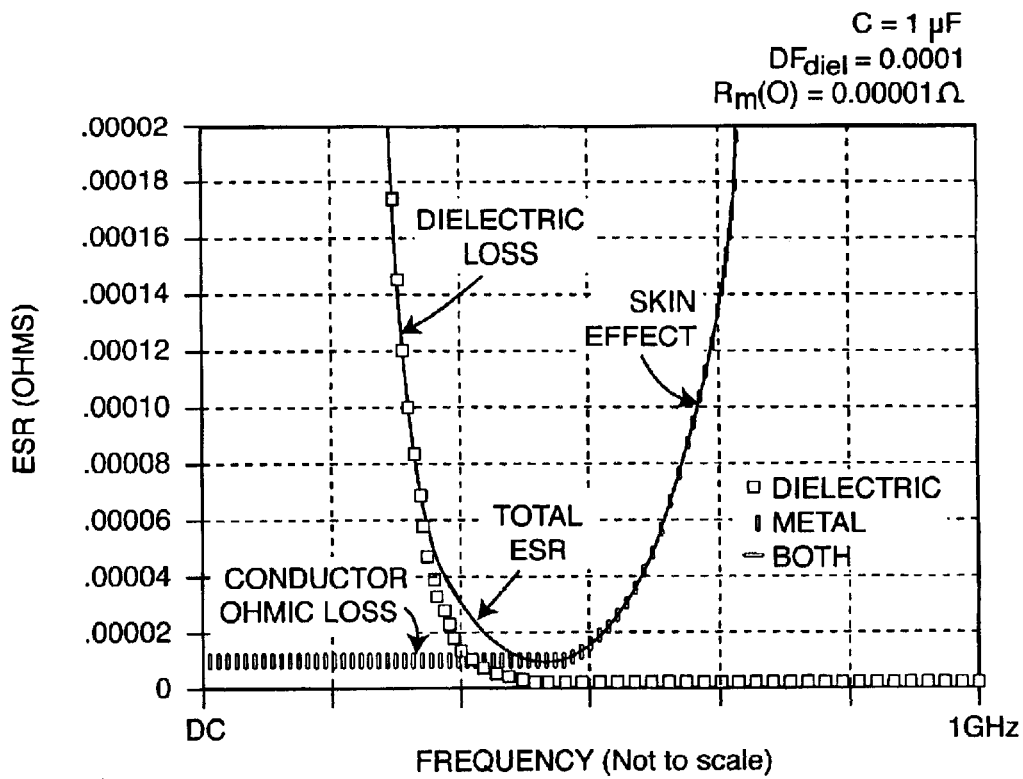
FIG. 10 is a graph illustrating normalized curves which show the capacitor equivalent series resistance (ESR) on the y axis, versus frequency on the x axis.
Figure 11:
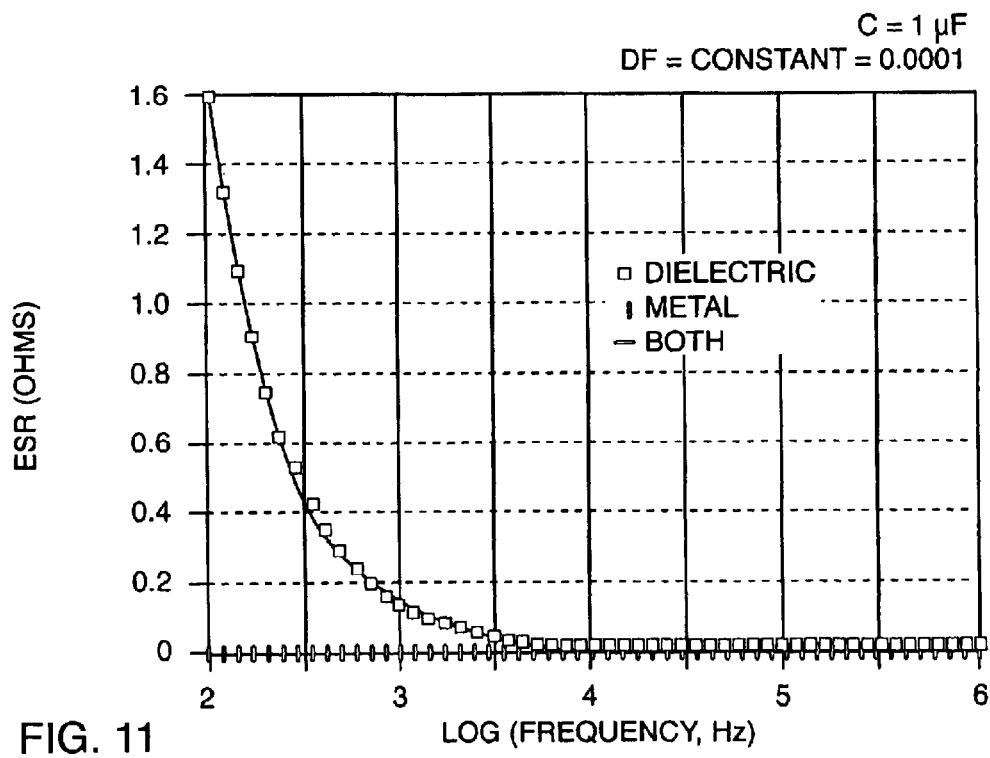
FIG. 11 is a graph illustrating dielectric loss versus frequency.
Figure 12:
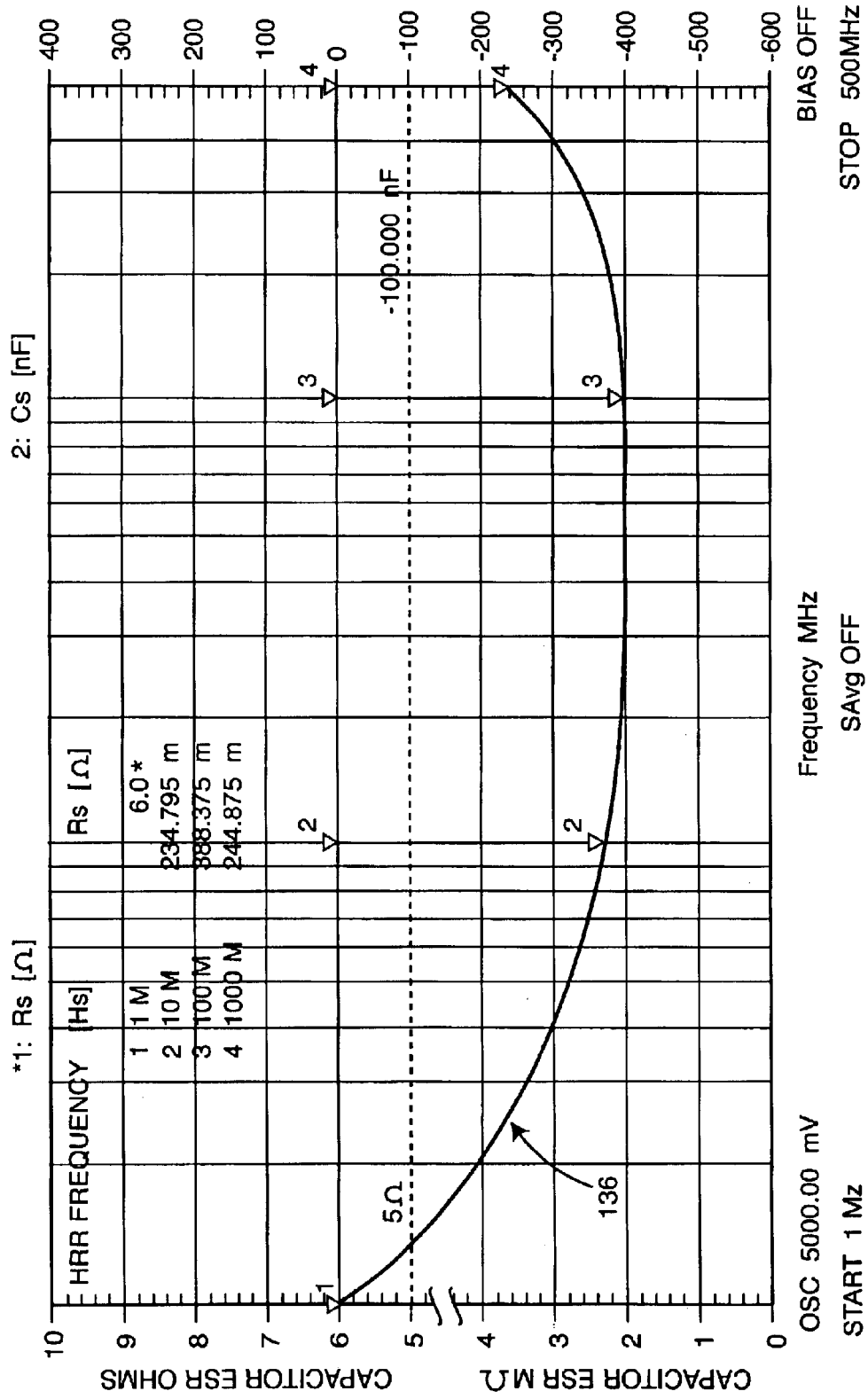
FIG. 12 is a graph illustrating capacitor equivalent series resistance versus frequency as illustrated in a sweep from an Agilent E4991A materials analyzer.
Figure 13:
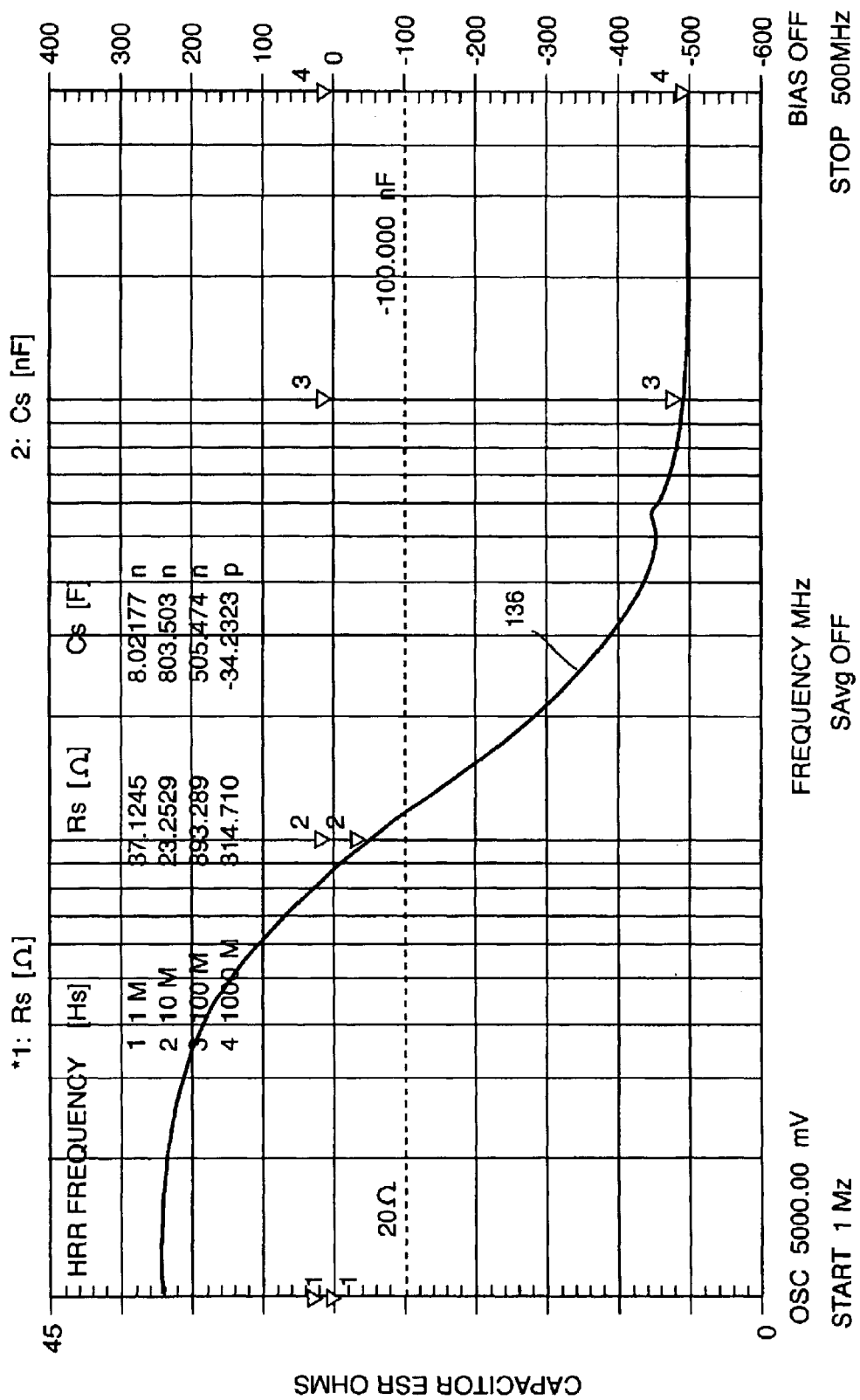
FIG. 13 is a graph similar to that shown in FIG. 12, illustrating the resistance in a feedthrough filter capacitor assembly when a substantial amount of titanium oxide is present on the ferrule.
Figure 14:
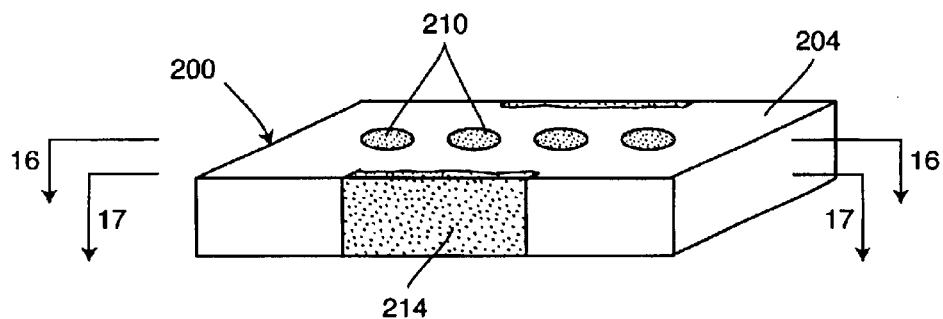
FIG. 14 is a perspective view of a rectangular broadband or low pass EMI filter capacitor.

Speaking specifically to U.S. Pat. No. 5,867,361 (Wolf, et al) dated Feb. 2, 1999, FIG. 1 of the Wolf patent discloses a gold braze 40 for connection of the conductive polyimide 47 to the titanium ferrule. Wolf indicates that the insertion loss or high frequency performance of the EMI filter is improved by connection to this gold bond pad. FIG. 9 illustrates the attenuation in decibels with and without a gold bond pad 40. In the Wolf patent, the hermetic seal is made between the alumina insulator using a gold braze shown in FIG. 1 as Item 15. The gold braze 15 connects between the ferrule 93 and the alumina insulator 25. There is also a hermetic and electrical connection made between the lead wire 29 and the alumina insulator through gold braze 90. It is significant that the entire hermetic seal is formed in this lower region of FIG. 1. The attachment to the filter capacitor 50 is made using conductive polyimide 47 which is attached to the ferrule 93 by way of the gold brazed material 40. In the Wolf patent, the gold braze material is an area completely separate and distinct from the gold braze material 15 which is used to form the hermetic seal. Accordingly, this is done in two operations or two steps involving two separate gold brazed pre-forms. There is no hermetic seal between the ceramic capacitor 50 and the ferrule 93. In fact, any material used to make electrical connection between the ceramic capacitor and the ferrule is described as a conductive thermalsetting material, such as a silver filled polyimide or a solder or the like. None of these are suitable biocompatible sealing materials for human implant applications and they certainly do not make a hermetic seal (nor does solder since it is not considered a biocompatible material).

It is a novel feature of the present invention, as shown in FIG. 22, that the hermetic seal and the gold bond pad is integrated into a single monolithic structure.

Figure 23:
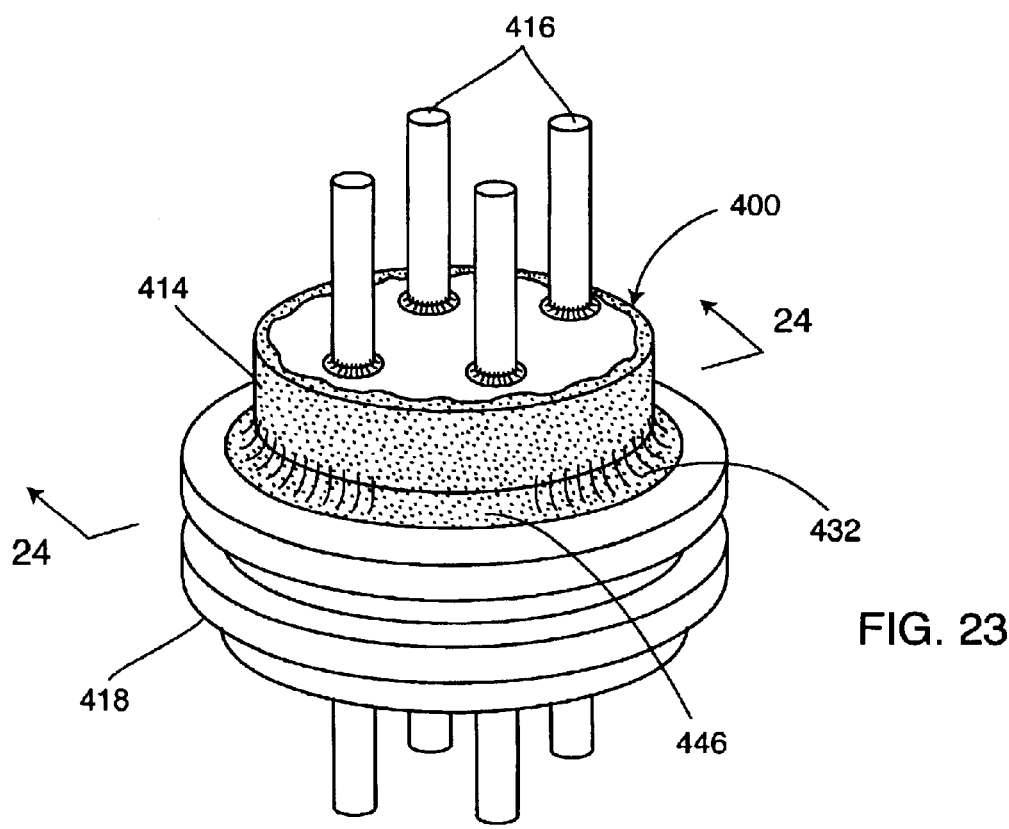
FIG. 23 is a perspective view of a surface mount round quadpolar feedthrough capacitor embodying the present invention.

FIG. 23 illustrates a surface mounted quadpolar feedthrough capacitor 400. A gold braze bond pad area 446 has been added to facilitate the connection between the capacitor outside diameter metallization 414 and the titanium ferrule 418. As mentioned before, this connection can be made as in the past with a thermalsetting conductive adhesive 432 or with solder or the like.

Figure 24:
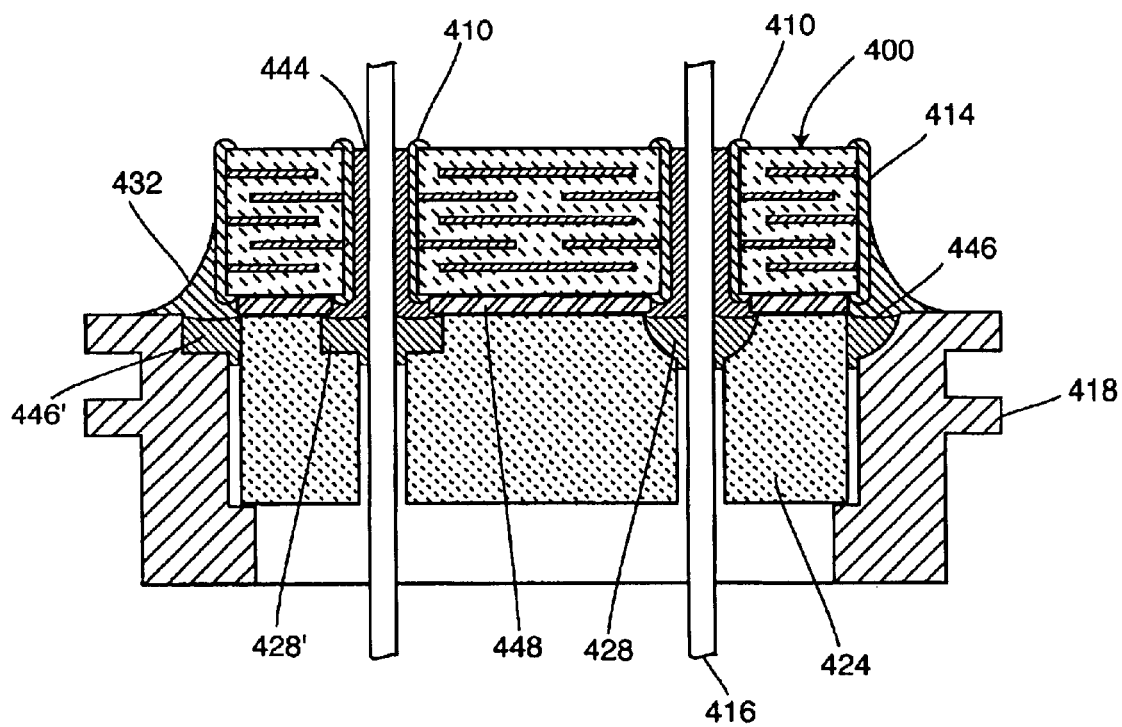
FIG. 24 is an enlarged sectional view taken generally along the line 24—24 of FIG. 23.

FIG. 24 is a cross-section of the quadpolar feedthrough filter capacitor terminal of FIG. 23. The gold braze area 446 or optionally 446' has been extended and widened so that the capacitor outside diameter electrical connection 432 will touch off between the capacitor outside diameter metallization 414 and the gold braze surfaces 446 or 446'. By having an electrically conductive metallurgical joint directly between the capacitor metallization and the gold braze, there is no chance for any titanium oxide build-up to affect the capacitor's performance.

Another inventive concept illustrated in FIG. 24 is the electrical connection 444 between the lead wires 416 and the capacitor metallization 410 and gold braze 428, 428'. This has been made possible by use of a thermalsetting insulative material 448.

A unique design constraint affecting filtered hermetic terminals for implantable medical devices is that these devices are designed to be welded into the overall titanium housing of a pacemaker, implantable defibrillator or the like. Accordingly, the feedthrough capacitor assembly is subjected to a great deal of heat and thermal stress. Thus, the insulative material 448 has to withstand very high temperature. One such insulative material 448 is a unique thermal plastic polyimide supportive tape (coated with thermalsetting adhesive) manufactured by Ablestik Electronic Materials and Adhesives, (the mechanical properties of which are listed in FIG. 25.) This material, which is known as Ableloc 5500, is unique in that it has the high temperature characteristics of a polyimide and yet will not flow. In other words, it stays in place, which allows one to form the novel structure shown at 448.

It is very important that the bottom or the surface between the capacitor 400 and the alumina insulator 424 be sealed so that conductive materials or fluids cannot run between the capacitor pins and short it out. The Ableloc 5500 is ideal in that it forms a seal while remaining in place. This means that for the first time the present invention can guarantee that the capacitor inside diameter connection can be between the capacitor metallization 410 and the gold braze 428 or 428', which opens up entirely new possibilities. For the first time niobium or tantalum pins can be utilized, without preparatory and secondary processing operations which are required because these materials are notoriously covered with oxide. No longer must there be a direct connection between the capacitor metallization 410 and the pin 416 itself. Instead, the gold braze 428 or 428', which forms the hermetic seal, makes an oxide free metallurgical and very low resistance connection to the pin itself (in a one step operation). Accordingly, the electrical connection 444 between the pin 416 as shown in FIG. 24 is actually from the capacitor inside diameter metallization 410 directly to the gold braze 428. The presence of oxides on the pin simply doesn't matter since a very low resistance electrical connection has already been formed. This electrical connection is also RF tight allowing the feedthrough capacitor to operate at very high frequency as a proper EMI filter.

Figure 26:
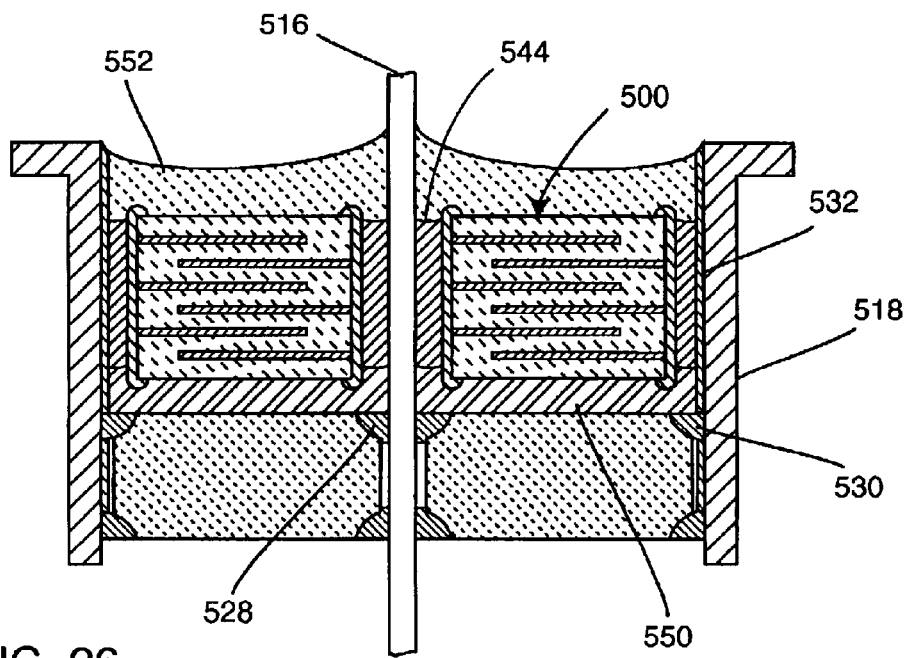
FIG. 26 is a sectional view similar to FIG. 24, illustrating a prior art feedthrough filter capacitor terminal typical of that shown in U.S. Pat. No. 4,424,551.

FIG. 26 represents a prior art feedthrough capacitor 500 typical of U.S. Pat. No. 4,424,551 and related patents. The bottom surface of the capacitor 500 has been flooded with a nonconductive epoxy 550. As exemplified in U.S. Pat. No. 4,424,551, the insulative material 550 is cured so that the capacitor 500 is bonded into the case 518. Subsequent to this, the entire surface above the capacitor 500 is flooded with conductive polyimide material 532, which is then centrifuged into place. It is very important during the centrifuge operation that material not flow underneath the capacitor thereby forming a short between the ferrule and the capacitor inside diameter pin 516. An optional insulative epoxy coating 552 could be added to cosmetically cover the surface of the capacitor 500 and offer it some degree of mechanical protection. As can be seen in this prior art assembly, there is no way for the conductive polyimide 544 at the inside diameter to reach the gold braze 528. Also, it is not possible for the outside diameter conductive polyimide 532 to reach the gold braze 530. This type of prior art assembly is sensitive to any type of titanium oxide build-up that may occur on the inside diameter of the titanium ferrule.

Figure 27:
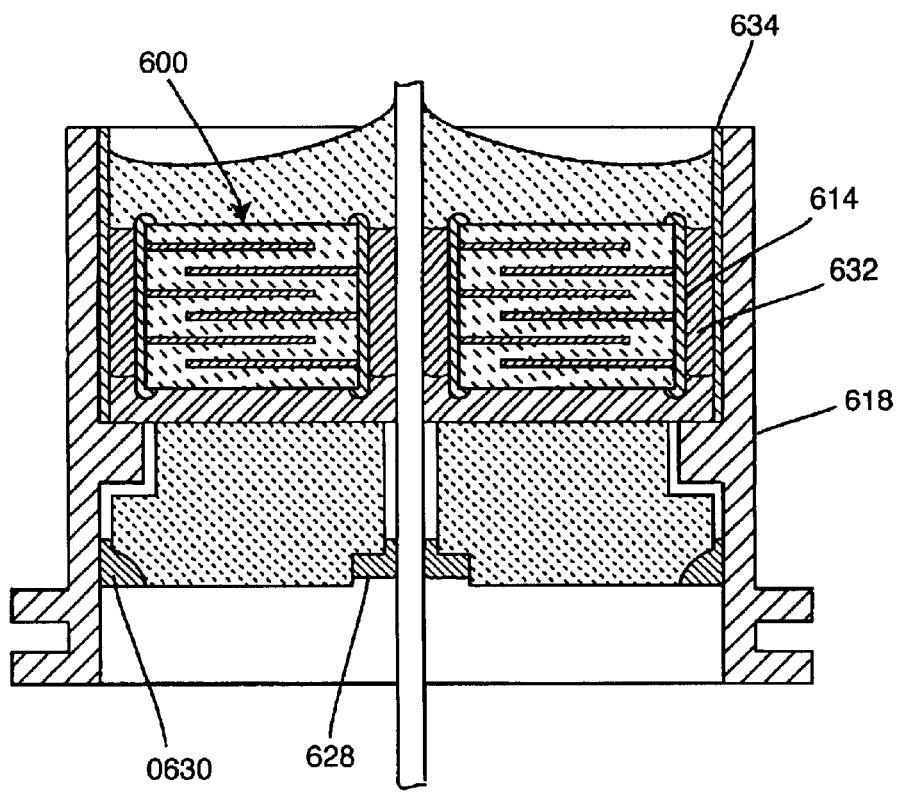
FIG. 27 is a sectional view similar to FIGS. 24 and 26, illustrating an alternative embodiment of a prior art feedthrough filter capacitor terminal.

FIG. 27 illustrates another prior art feedthrough capacitor 600 and related structure. This unit has a substantial oxide layer 634 on the inside of the titanium ferrule 618. For simplicity, this oxide layer is only shown on the inside diameter of the ferrule 618 where the electrical connection to the capacitor ground metallization 614 is made (in actual practice, the oxide would to some degree coat all of the ferrule surfaces). Accordingly, there will be a high resistance between the conductive polyimide 632 and the titanium ferrule 618. In this case the gold brazes 628 and 630 are shown on the opposite side away from the feedthrough capacitor 600. Accordingly, there is no way in this structure for the feedthrough capacitor ground polyimide connection to have contact with the gold braze 630. Thus, this prior art assembly is subject to EMI filter performance degradation if the oxide layer becomes too thick. Product life is another concern. Oxides can build up very slowly over time and lead to a latent type of design defect.

Figure 28:
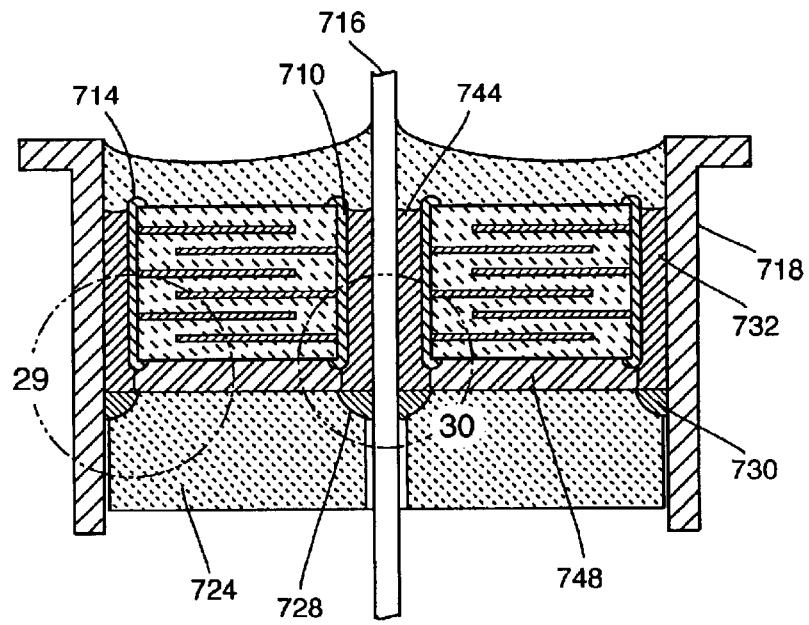
FIG. 28 is a sectional view similar to FIGS. 26 and 27, and further illustrating application of the present invention.

FIG. 28 illustrates the novel technology of the present invention as applied to the basic structures illustrated in FIGS. 26 and 27. The unique Ableloc 5500 or equivalent high temperature thermal plastic polyimide supportive tape 748 allows the nonconductive insulating material to be held in place as shown (B staged epoxy washers could also be used, however, their temperature rating is not as high). This allows clear access for the conductive polyimide 744 or 732 to penetrate and contact the gold braze area 746. In this case, it is important that the gold braze be on the capacitor side of the insulator 724. The assembly shown in FIG. 28 no longer requires that the pin(s) 716 be restricted solely to platinum iridium or other non-oxidizing materials. This allows the use of much lower cost niobium or tantalum pins. The electrical connection can be between the capacitor inside diameter metallization 710 directly to the gold braze 728 itself. Accordingly, there is no need for an electrical connection between the capacitor inside diameter metallization 710 and the lead wire 716 at all. It can also be clearly seen in FIG. 28 that it would not matter if the inside diameter of the ferrule 718 was heavily oxidized. This is because there is an electrical connection directly from the capacitor outside diameter metallization 714 to the outside diameter gold braze 730.

Figure 29:
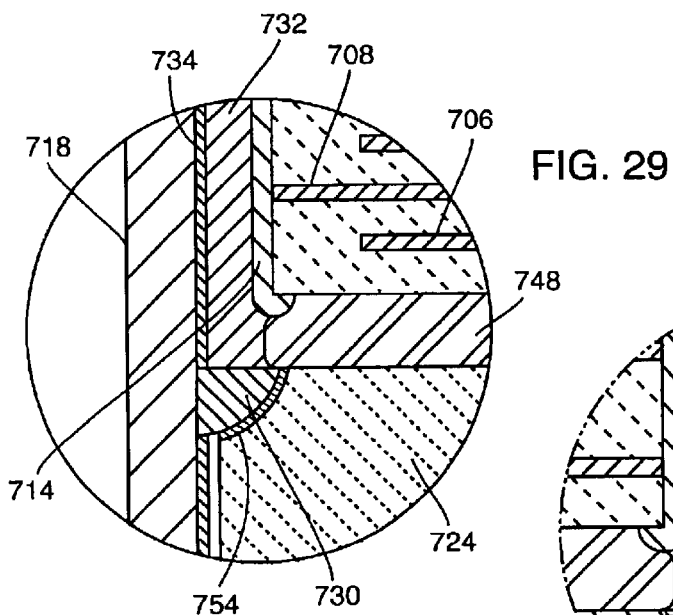
FIG. 29 is an enlarged view of the area indicated by the number 29 in FIG. 28.

FIG. 29 is a broken out enlarged view of the outside diameter connection of FIG. 28. As one can see, there is an oxide layer 734 which would tend to insulate the conductive polyimide or solder 732 from the titanium. However, because of the proper location of insulative material 748, the conductive polyimide, solder or the like 732 can make direct contact between the capacitor metallization 714 and the gold braze area 730. Sputtering 754 of metals on the alumina insulator 724 are required before the gold braze hermetic seal typically can be formed. This allows the gold braze material 730 to wet to the alumina insulator 724 and form a hermetic seal.

Figure 30:
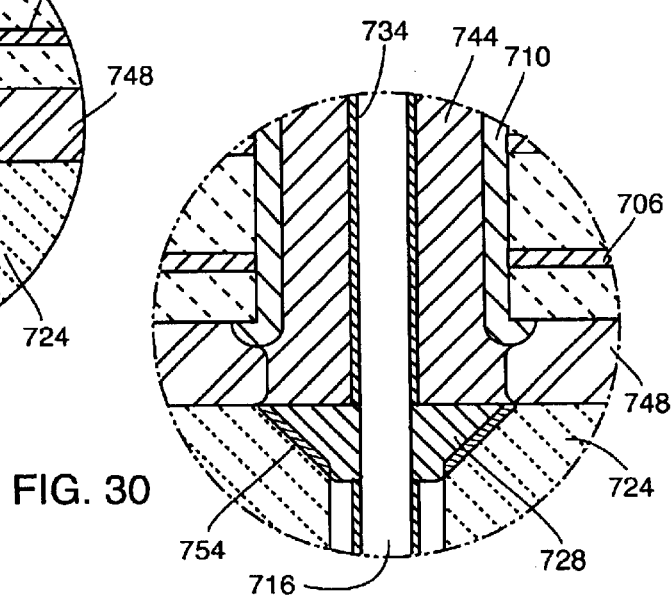
FIG. 30 is an enlarged view of the area indicated by the number 30 in FIG. 28.

FIG. 30 is an enlarged view of the electrical connection to the lead wire 716 of FIG. 28. It is assumed that a type of lead wire is used, such as tantalum or niobium, which would be heavily oxidized 734. Not only are these oxides highly insulative, but they also do not form a solderable surface. However, a feature of the invention is that during hermetic seal construction, the oxides are absorbed by the metallurgical bond formed between the gold braze area 728 and the pin 716. This is the same gold braze that forms the hermetic seal to the alumina insulator 724. A sputtered layer 754 allows the gold to wet to the insulator 724. As one can see, no direct connection between the capacitor metallization 710 and the lead wire 716 is required. Instead, the connection to the capacitor is accomplished by the thermalsetting conductive adhesive or solder 744 which connects from the capacitor metallization 710 directly to the gold braze 728. Since the gold braze 728 has a metallurgical low resistance and low impedance connection to the pin, no further connection is required. In the case of a non-oxidizing pin material such as platinum, gold or platinum-iridium alloy, it is not necessary to form the structure as illustrated in FIG. 30. In other words, the insulative washer 748 could extend all the way across the inside diameter thereby blocking access to the gold braze.

The most critical element in a medical implant feedthrough design (that must remain hermetic throughout it's device service life) is the metal/ceramic interface. Important are the nature of the bond itself and the sensitivity of the bond integrity to environmental conditions imposed as a result of the device fabrication process (like installation by laser welding by the pacemaker manufacturer) or as a part of environmental conditions developed while in service (body fluid is highly corrosive). For a braze-bonded feedthrough, the bond needs to deform in a ductile manner when environmental conditions create stresses (e.g., heating and cooling cycles that develop during device assembly welding). Typically, metallization and braze material combinations develop alloys that solidify as intermetallics. These intermetallics often show only modest ductility prior to failure. If material combinations are not judiciously selected and processes are not understood and controlled, significant dissolution can occur, and brittle fracture of the bond, or latent failures (static fatigue) result compromising hermetic integrity of the feedthrough.

A unique challenge for formation of the novel bond pads of the present invention is that they are formed as an integral part of the hermetic seal joint. This requires a relatively large amount of gold braze material (or other noble metal) to be used. In prior art EMI filtered human implant hermetic seals, the volume of braze material is by design relatively small. In the present invention, with the larger volume of braze material that is required, higher stresses due to shrinkage and mismatches in the thermal coefficient of expansion (TCE) of the braze material become a major design challenge. The biggest concern is the added stress in tension or shear which is transmitted to the metallic layer on the alumina hermetic seal/insulator (this layer is what allows the braze material to wet to the alumina and form the hermetic seal and is preferably applied by sputtering or equivalent methods). Unfortunately, the TCE of the high alumina content ceramic insulator does not match the TCE of any of the noble metal braze materials. Accordingly, for formation of the novel integrated gold hermetic seal/bonding pad as described herein, a unique metallization is required to be used in combination with the present invention that has high malleability and very high adhesion strength to the alumina ceramic and will also wet well to the braze material. It is a feature of the present invention that the preferred metallization on high alumina ceramics for miniature medical implantable device hermetic terminals, is titanium/molybdenum. Titanium is the active layer, and molybdenum is the barrier layer controlling how much titanium can actually dissolve in the gold. For example, 2–4 microns of titanium can be sputtered followed by 2–4 microns of molybdenum. The thickness will be dependent on the design, the application, and the subsequent potential environmental exposures. In this example, the titanium layer provides the interaction with the glass phases and alumina particle matrix of the ceramic to create a hermetic bond. The molybdenum layer protects the titanium layer from excessive oxidation prior to brazing and acts as a barrier between the gold braze material and the titanium layer. Without the molybdenum barrier layer, an excessive length of exposure of the titanium layer to the molten gold would accelerate the inherent alloying process and eventually lead to de-wetting, then hermetic failure The titanium/molybdenum metallization in concert with gold braze, therefore, not only provides a sound hermetic bond, but also provides a sufficiently ductile materials feedthrough system to sustain secondary device assembly processes or environmental conditions that might develop stresses while the device is in service.

Other metallization materials that can be used with gold braze materials include but are not limited to titanium, niobium, chromium, zirconium, or vanadium active materials with molybdenum, platinum, palladium, tantalum or tungsten barrier layers in various combinations. Sputtering is one metallization application method. Other methods that might be used include but are not limited to chemical vapor deposition, laser or other physical vapor deposition processes, vacuum evaporation, thick film application methods, plating, and so on.

FIGS. 31–36 illustrate an internally grounded bipolar rectangular feedthrough capacitor 800 as described in U.S. Pat. No. 5,905,627. The center hole is the grounded hole 858 which would connect to the capacitor internal electrode plates 808. More specifically, the feedthrough filter capacitor 800 comprises a monolithic, ceramic internally grounded bipolar feedthrough filter capacitor having three passageways extending therethrough. The outer two passageways 856 are configured to receive therethrough respective conductive terminal pins 816' and 816", and the internal diameter of the first passageways 856 are metallized 810 to form a conductive link between the active electrode plates 806. As is well understood in the art, the active electrode plates 806 are typically silk-screened onto ceramic plates forming the feedthrough filter capacitor 800. These plates 806 are surrounded by an insulative ceramic material 804 that need not be metallized on its exterior surfaces.

Similarly, ground electrode plates 808 are provided within the feedthrough filter capacitor 800. The inner diameter of the central or second passageway 858 through the feedthrough filter capacitor 800 is also metallized 811 to conductively connect the ground electrode plates 808, which comprise the ground plane of the feedthrough filter capacitor 800. The second passageway 858 is configured to receive therethrough the ground lead 860 which, in this particular embodiment, comprises a ground pin.

With reference to FIG. 32, the terminal pin subassembly comprises a plate-like conductive ferrule 818 having three apertures therethrough that correspond to the three passageways through the feedthrough filter capacitor 800. The conductive terminal pins 816' and 816" are each supported through the outer apertures by means of an insulator 824 (which also may be hermetic), and the ground pin 860 is supported within the central aperture by a suitable conductor 830 such as gold brazing, solder, an electrically conductive thermalsetting material or welding/brazing.

Figure 35:
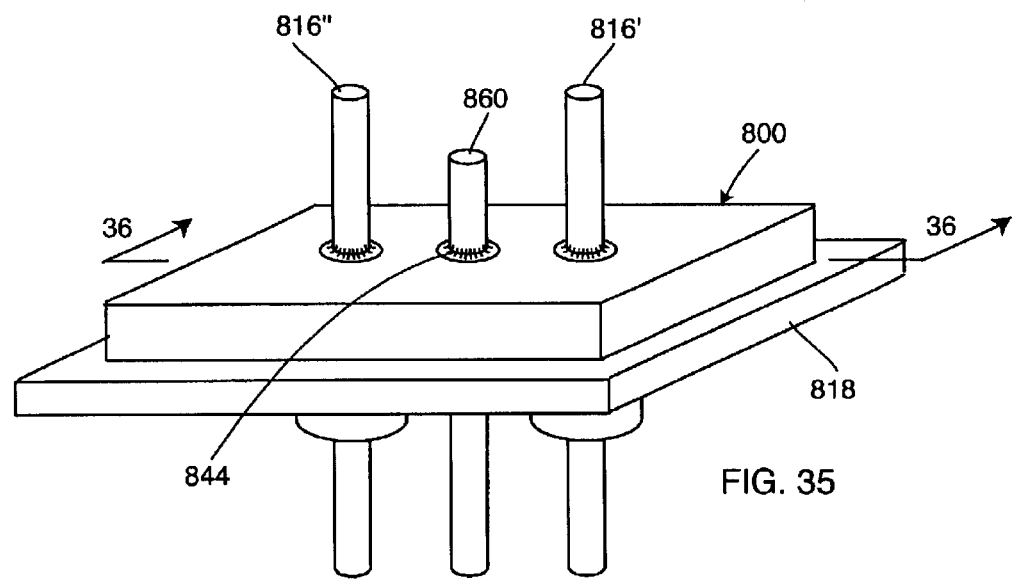
FIG. 35 is a perspective view of the internally grounded bipolar feedthrough capacitor of FIG. 31 mounted to the hermetic feedthrough terminal of FIG. 32.

The feedthrough filter capacitor 800, as shown, is placed adjacent to the non-body fluid side of the conductive ferrule 818 and a conductive attachment is effected between the metallized inner diameter of the first and second passageways 856 and 858 through the feedthrough filter capacitor 800 and the respective terminal pins 816 and ground lead 860. Alternatively, the capacitor 800 could be placed adjacent to the body fluid side of the conductive ferrule 818 provided the capacitor comprises a design incorporating biocompatible materials. In FIG. 35, the conductive connections 844 between the terminal pins 816 and the ground lead 860, with the feedthrough filter capacitor 800 may be effected by any suitable means such as a solder or an electrically conductive thermalsetting material or brazing. The result is the feedthrough filter capacitor assembly illustrated in FIGS. 35 and 36 which may then be subsequently laser welded into the titanium housing of an implantable medical device.

FIG. 35 illustrates the internally grounded bipolar feedthrough capacitor 800 of FIG. 31 mounted to the hermetic feedthrough terminal 802 of FIG. 32. The ground lead 860 can be shortened so that it does not protrude through the capacitor 800 or it can be lengthened depending on whether or not a circuit attachment is required within the implantable medical or other electronic device. If the lead wires are solderable (platinum or gold), then the connection between the lead wires and the capacitor inside diameter metallization can be accomplished using solder, conductive adhesive or the like. A feature of the internally grounded feedthrough capacitor 800 is that no outside diameter (or perimeter in the case of FIG. 35) electrical connection or capacitor metallization is required.

Figure 36:
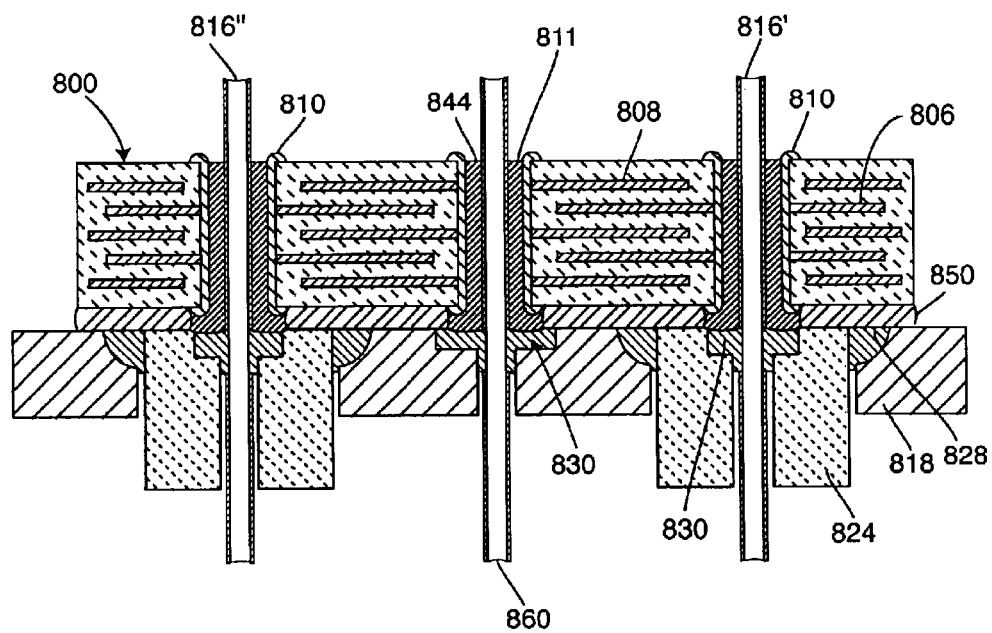
FIG. 36 is a cross-sectional view taken generally along the line 36—36 of FIG. 35.

FIG. 36 is a cross-section of the capacitor assembly of FIG. 35. This illustrates several novel features of the present invention that are applicable to the internally grounded feedthrough capacitor, especially when lead wire materials that are subject to oxidation are used (such as niobium or tantalum). As one can see, the thermal plastic polyimide supportive tape 850 has been carefully punched, die-cut, or laser cut to align with the capacitor such that the capacitor feedthrough holes are open to the gold braze material 830 underneath. This allows a direct connection of the solder or conductive polyimide 844 to connect directly between the capacitor metallization 810, 811 and gold braze material 830. Accordingly, this opens up a wide variety of lead materials for use, which could not be considered before due to their heavy oxidation or poor solderability properties. This also allows the use of a ground pin of alternate materials, like titanium. A titanium ground pin is desirable because it is very easy to weld a titanium pin into a titanium ferrule. In the past, it was not possible to solder directly to titanium, however, a feature of the present invention is the capability of connection to the gold braze area. It should be apparent that not all leads are required to be constructed of the same material. For example, the center (ground) lead 860 could be titanium and the two active pins 816' and 816" could be platinum. In this case, it would not be required that conductive material 844 adjacent the platinum pins 816' and 816" contact the gold braze 830.

Figure 37:
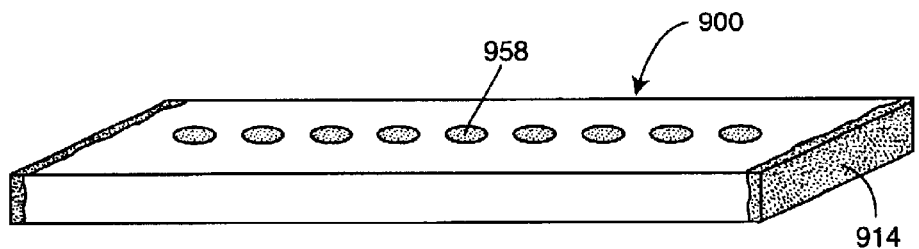
FIG. 37 is a perspective view of a hybrid capacitor which has the characteristics of a conventional surface-mounted feedthrough capacitor and an internally grounded capacitor.
Figure 38:
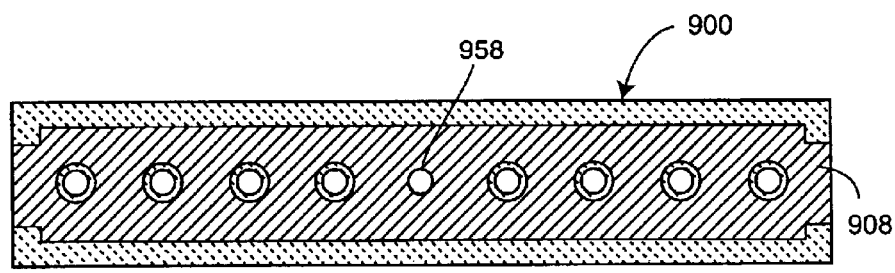
FIG. 38 is a horizontal section through the capacitor of FIG. 37, illustrating the configuration of the ground electrode plates therein.
Figure 39:
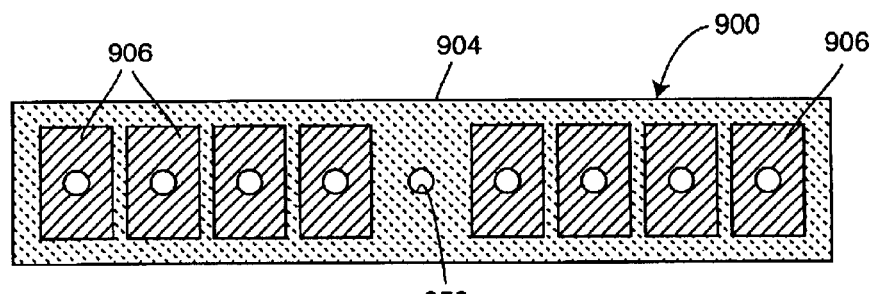
FIG. 39 is a horizontal section similar to FIG. 38, illustrating the configuration of the active electrode plates therein.

FIG. 37 illustrates a novel hybrid capacitor 900 which has the characteristics of a conventional surface mounted feedthrough capacitor and an internally grounded capacitor. This capacitor 900 has a ground hole 958 in the center which connects to the internal ground electrode plates 908 and also has ground terminations 914 at either end. The reason for this is that this capacitor has a form factor which tends to increase its inductance and impedance. Accordingly, if one were to only make connection to the ground electrodes 908 shown in FIG. 38 at the center hole 958, there would be too much inductance between this and the outer pins to perform effective EMI filtering. This hybrid design is best illustrated by the ground electrode plate pattern as shown in FIG. 38, wherein the ground electrode 908 is attached to the titanium ferrule 918 at both the right and left ends and also in the middle. This guarantees that the capacitor 900 will have very low impedance across its entire ground plane thereby ensuring that it will work properly as a high frequency EMI filter. FIG. 39 is an illustration of the active electrode plate pattern 906.

Figure 40:
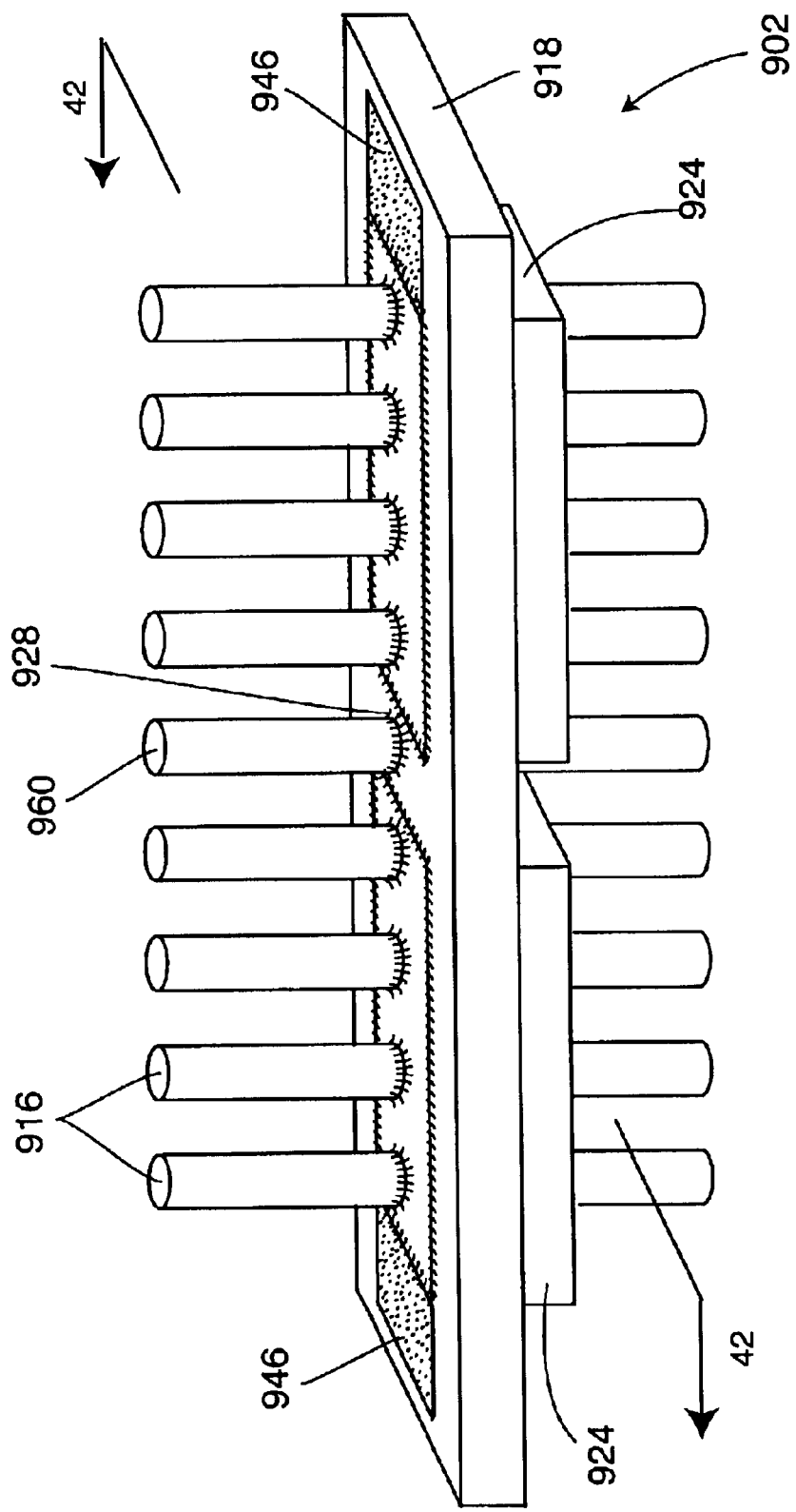
FIG. 40 is a perspective view of an hermetic terminal designed for use in connection with the capacitor illustrated in FIGS. 37–39, the terminal including a titanium ferrule.

FIG. 40 illustrates the simplified hermetic terminal 902. The centered ground pin 960 is welded or brazed 928 directly to the ferrule 918. This forms a low resistance and low inductance ground connection to the pin 960. The other pins 916 are shown in insulative relationship with the ferrule 918. The novel gold bond pads of the present invention are shown as 946. Restated, the ground pin 960 has been solidly brazed directly to the ferrule 918. This provides a very low impedance RF ground between the center pin 960 and the overall electromagnetic shield. One can also see in FIG. 40 that the gold bond pads 946 have been added on either end to form a convenient surface for the electrical connection between the capacitor end terminations 914 and the ferrule 918. It can also be seen that the other four pins 916 on both the right and left sides of the capacitor 900 are in electrically insulative relationship. This is done through the insulators 924 which can be glass or a gold brazed alumina seal.

Figure 41:
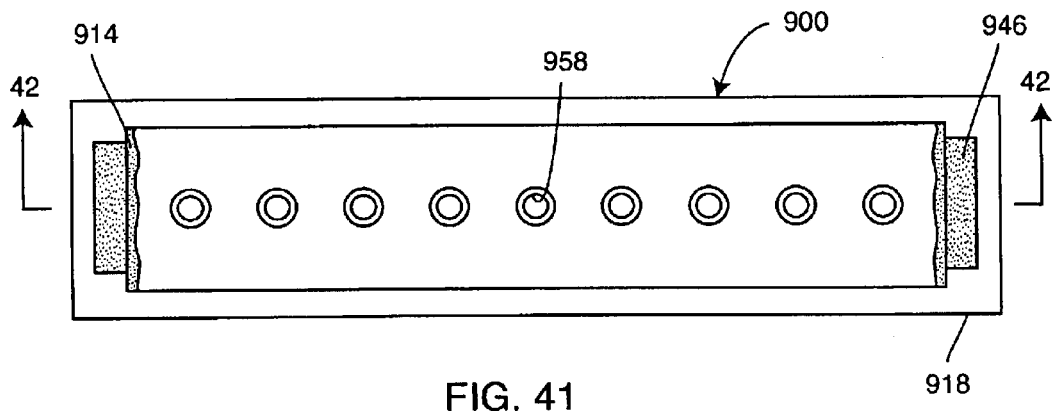
FIG. 41 is a top plan view of the capacitor of FIG. 37 mounted to the hermetic terminal of FIG. 40.

FIG. 41 is a top view of the capacitor of FIG. 37 mounted to titanium ferrule 918. The novel gold braze ground pads 946 of the present invention have been added so that an oxide free electrical connection can be made between the capacitor-ground terminations 914 and the conductive ferrule 918.

Figure 42:
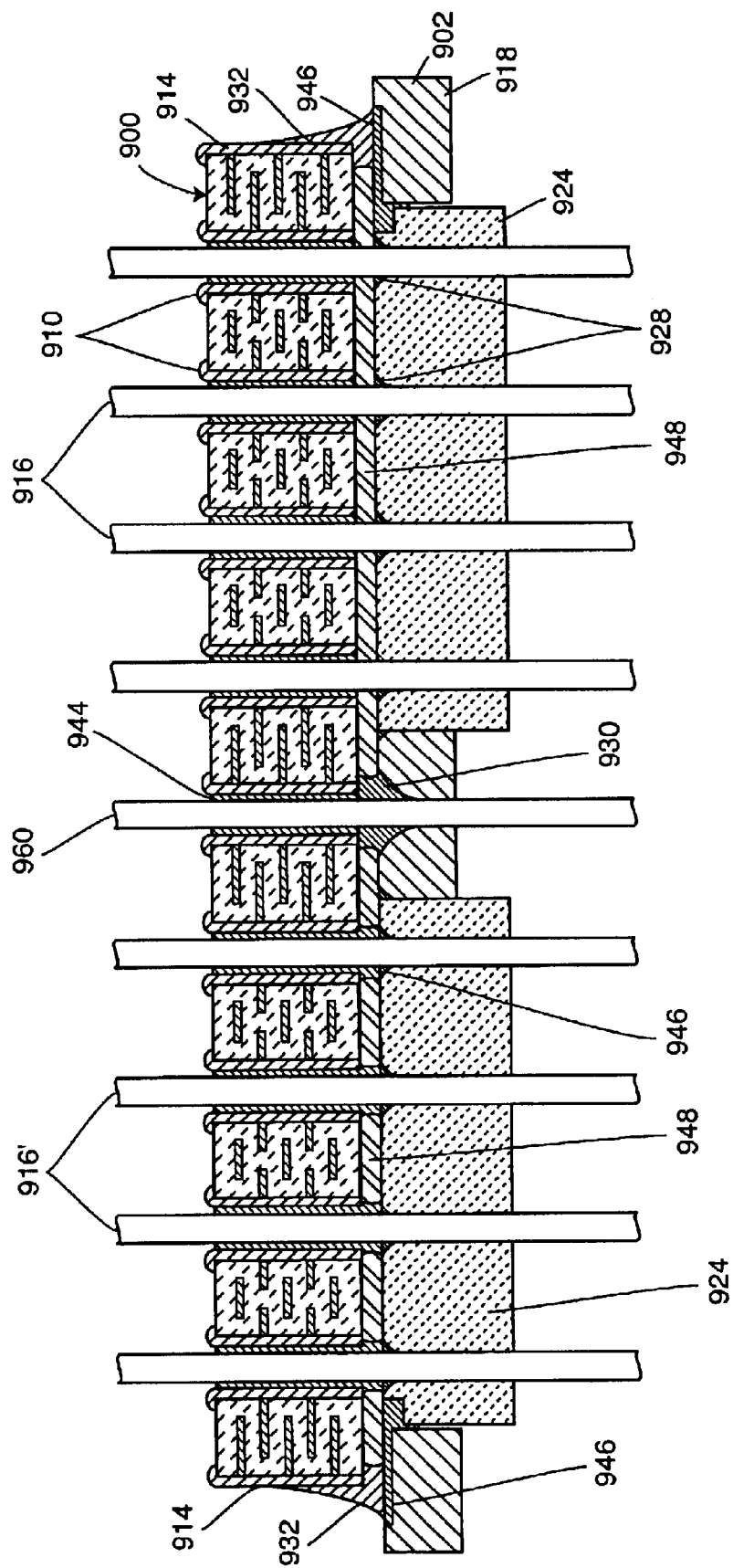
FIG. 42 is a sectional view taken generally along line 42—42 of FIG. 41.

FIG. 42 is a cross-sectional view of the capacitor 900 assembled to the hermetic terminal 902 of FIG. 40. As shown, the gold bond pads 946 are also part of a single monolithic structure forming the hermetic seal between the ferrule 918 and the insulator 924, in the same manner and for the same reasons as discussed above in connection with FIG. 22. The connection between the capacitor ground metallization 914 (at its two ends) and the gold bond pads 946 is shown as material 932, which can be solder, conductive thermalsetting material, or the like. The connection to the centered ground pin 960 is illustrated by material 944 which can also be solder, conductive thermalsetting material, or the like. As previously mentioned, in the present invention it is desirable to form insulative material 948 such that the electrical connecting material 944 adjacent to the ground pin 960 will directly contact the gold braze 928. This is particularly important for ground pin lead materials that are not readily solderable or that form insulative oxide layers. The novel gold bond pad area 946 as previously mentioned could also be accomplished by sputtering, plating and the like.

As illustrated in FIG. 42, for comparison purposes, the hermetic terminal 902 includes two distinctly different sets of lead wires 916. To the left of the ground pin 960, the lead wires 916 are shown as comprised of low cost niobium or tantalum pins on which heavy oxides typically form. When utilizing such low cost pins, the pads of oxide resistant conductive biostable material, noble metal, or the like, 946 are utilized to provide both a hermetic seal between the pins and the insulator 924, and also to provide a reliable electrical connection between the interior termination surfaces 910 and the leads 916, as discussed above in connection with FIGS. 24, 28-30 and 36. In contrast, the lead wires 916 to the right of the ground pin 960 are all platinum. As a noble metal, platinum is not subject to oxidation. Accordingly, it is not necessary for the solder or conductive polyimide used to connect between the capacitor inside diameter metallization and the lead wire to also contact the gold braze material 928. In other words, an oxide free electrical connection has already been made between the capacitor inside diameter metallization 910 and the lead wire 916, therefore it is not necessary to modify this assembly to contact the gold braze. However, in accordance with the invention, the aforementioned polyimide supportive tape 948 or the like could be placed to allow direct contact from the ground pin 960 to the gold braze 930 thereby allowing the use of a ground lead wire such as titanium, niobium or tantalum.

Figure 43:
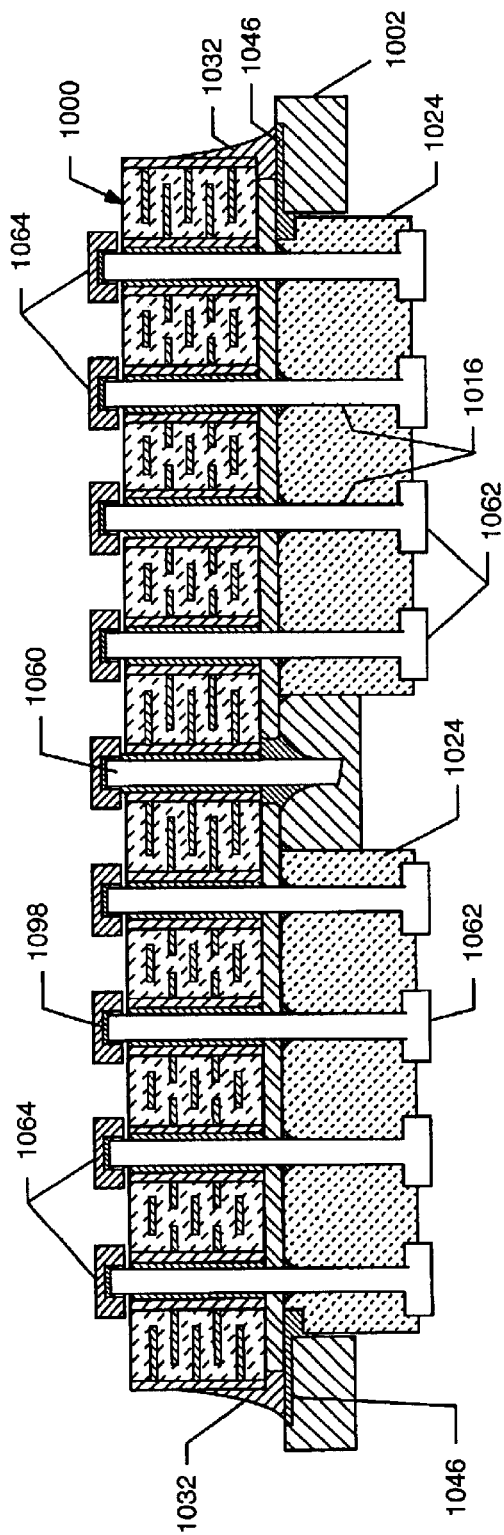
FIG. 43 is a sectional view similar to FIG. 42, illustrating a hybrid capacitor which has a centered ground pin and which is also grounded at its right and left ends to gold bond pads.

FIG. 43 shows a hybrid capacitor 1000 which has a centered ground pin 1060 and, because of its length and the desire to reduce inductance, is also grounded at its right and left ends using conductive polyimide 1032 to the gold bond pads 1046. This is a hybrid in that it incorporates the features of both U.S. Pat. Nos. 5,333,905 and 5,095,627. FIG. 43 illustrates novel wire bond pads that overcome all of the obvious deficiencies of the aforementioned Wolf patent. The preferred location for the hermetic braze between the insulators 1024 and the hermetic terminal 1002 is at the pads 1046. This takes the gold braze away from the body fluid both at each terminal pin and also at the hermetic seal joint to the ferrule. When a header block, which is commonly used in the industry is attached, silicone or other material is utilized which will fill the space between the lead all the way down to the gold braze. This effectively blocks the ready access of body fluids to the gold braze thereby preventing reverse electroplating involving material deposition to some other surface in the presence of a voltage bias. In other words, the location of the hermetic seal shown in FIG. 43 will overcome any problem with long term exposure to body fluid.

Figure 44:
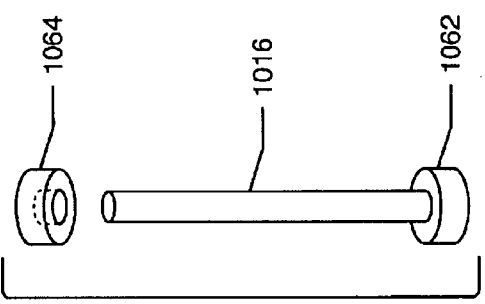
FIG. 44 is an enlarged, perspective and partially exploded view of one of the terminal pins shown in FIG. 43.

FIGS. 43 and 44 further illustrate an extruded nail head lead 1016 of bio-compatible material such as a noble metal including platinum, platinum iridium, gold and the like. The nail head portion 1062 of the lead 1016 on the bottom or body fluid side could be extruded as one piece particularly with a malleable material welded in place, brazed in place, or adhesively secured in place to the lead 1016. The capacitor 1000 is attached to the terminal 1002 using similar processes as described above, and the leads 1016 are attached at the time that the hermetic seal joint 1046 is formed. During capacitor attachment the leads 1016 are allowed to stick through the capacitor 1000 as shown. At this point there are a number of options for the assembly. One option would be to make a solder joint, braze, weld or a thermalsetting conductive adhesive joint 1099 between the capacitor inside diameter termination and the nail head terminal pin 1016. One could then add a wire bond closed pad or cap 1064 and attach it by soldering, welding, thermal conductive adhesive brazing or the like 1098. The wire bond pad 1064 does not need to be bio-compatible and could be made of a number of inexpensive materials including nickel, copper, steel and the like. For wire bond applications it is usually required that the wire bond pad 1064 be pure (soft) gold plated, but a number of other surface finishes can be applied as well. The wire bond pads/nail head assembly 1016, 1064 could also be formed from the group of metals including: tantalum, molybdenum, titanium, rhodium, titanium alloys, osmium, silver and silver alloys, vanadium, platinum, niobium, platinum alloys, stainless steel, tungsten, rhenium, zirconium, vanadium and ruthenium.

FIG. 45 illustrates an internally grounded hex polar capacitor 1100 embodying the invention (refer to U.S. Pat. No. 5,905,627). In this particular device, the novel wire bond pads 1164 as previously described have been utilized. The nail head pin 1116 is of the same group of materials as previously described for FIG. 43. However, in this embodiment the hermetic seal 1146 has been moved to an alternate location and is now closer to exposure to body fluids. This is also acceptable to many customers but is not the preferred embodiment for maximum resistance to long term decomposition by metal migration.

The wire bond pad 1164 on the inside of the implantable medical device has also been modified so it has an open hole. In this case this a ring structure which is slipped over the bio-compatible pin 1116 and then attached by soldering, welding, brazing, or thermalsetting conductive adhesive or the like. An advantage of this structure is it is a little bit easier to assemble and inspect. A disadvantage is that the area available for customer attachment of their lead wires by ultrasonic wire bonding, thermal sonic welding or direct welding has been reduced. In other words there is less flat surface area available for customer lead attach.

Referring to FIG. 47A, a different embodiment of attachment of the lead wire 1160 is shown. In this case the lead wire 1160 extends through a toroidal ring 1164' which may be constructed of various materials from the group of metals, and ceramics. One preferred embodiment would be the use of alumina ceramic which was metallized. This would allow one to form the electrical connection shown while at the same time allowing the lead wire 1160 to protrude through. In this case the very end of the lead wire 1160 could be the wire bond pad itself. There are a number of supplementary processes available after the extrusion of this lead wire to provide a flat and parallel surface. This has a number of advantages that will be obvious to one skilled in the art including the ability to readily inspect the joints.

More particularly, the preferred metallized alumina toroidal ring 1164' has been metallized on all surfaces so it is both solderable and conductive. Solder, thermalsetting conductive adhesive, welding or the like 1168 performs an electrical connection between the circular torroid 1164' which in turn connects to the capacitor 1100 active electrode plates 1106. In addition, material 1170, which can be of the group of solder, thermalsetting conductive adhesives, welding, brazes or the like, forms the electrical connection between the lead wire 1160 to the torroidal structure 1164' which then couples through the electrical connection 1168 via the capacitor metallization 1110 to the electrode plates. As shown the tip of the lead wire 1172 is flat to accept lead attachment by the customer by wire bonding, thermal sonic bonding, laser welding or the like. A supplementary nail head or enlarged area could be added to the tip 1172 to increase the surface area available for such customer lead attachment operations. One particular advantage of the structure shown in FIG. 47 is the ability to select a material that closely matches a thermal co-efficient expansion of the ceramic capacitor 1100. Such materials include fosterite, zirconium, gold alloys, or materials such dumet.

Capacitor 1100 has inside diameter metallization 1197 at each of the seven inside diameters to make electrical connection to the ground and active electrode plate sets. This metallization also appears on top of the capacitor as a circular mounting/bonding pad 1199. In this case, there is no need to fill the space between the capacitor inside diameters and the noble metal lead wires with an electrical connection material.

FIG. 47B shows that the lead wire and its electrical connection may be subflush or below the top of the ring pad 1164. In this case, the ring pad forms the wire bond surface.

As shown in FIG. 47C, the electrical connection is formed between pin 1116 and the capacitor top metallization 1199 using solder, braze, conductive adhesive or the like. Alternative connections using a variety of wire bond pad end caps are shown in FIGS. 47A, 47B, and 47C.

FIGS. 48 and 49 show an externally grounded quadpolar device. While a compatible nail head pin 1216 is utilized and in this case, the hermetic seal connection 1246 between the alumina ceramic 1224 and the nail head pin 1216 is in the preferred location. Drawing attention now to the wire bond end cap 1264, a different attachment method is contemplated. This attachment method is desirable in that it completely eliminates the necessity for any contact materials or any solder or other materials to be placed between the lead wire 1216 and the inside diameter termination of the ceramic capacitor 1200. In this case the capacitor 1200 inside diameter metallization 1210 is also formed as a circular structure on the top surfaces of the ceramic capacitor. This is commonly used in the connector industry and with planar arrays. Such structures are normally printed on the top surface of the ceramic capacitor by silk screening processes or the like. Accordingly, it is easy to form this on the top surface of the capacitor 1200. This makes the attachment of the end cap 1264 very simple and easy to facilitate in a manufacturing operation. As best seen in FIG. 49, attachment of the wire bond cap 1264 is simply accomplished by making a solder joint, conductive thermalsetting adhesive joint, braze joint, weld joint or the like shown as 1266. This makes a direct connection to the capacitor termination 1210. Accordingly, there is no other connection to the capacitor inside diameter that is needed. At the same time that the joint 1266 is formed or at a different time, the electrical connection 1299 to the end cap 1264 is also made. As previously mentioned, this can be done thermalsetting conductive adhesives, solder, brazes, welds or the like.

This is a major advantage over the aforementioned Wolf patent in that the inside diameter of the capacitor does not have any materials that mis-match it in its thermal co-efficient of expansion. Accordingly, the capacitor will be mechanically more rugged and more resistant to thermal shock such as those induced by the customer during installation by laser welding. The capacitor termination materials are preferably in this case formed from either plating or a fired on silver or a palladium-silver glass frit. These are put on as a thick film process sufficient so that it forms a mechanically rugged and electrically reliable attachment to the capacitor active electrode plates 1206.

Although several embodiments of the invention have been described in detail for purposes of illustration, various modifications of each may be made without departing from the spirit and scope of the invention. Accordingly, the invention is not to be limited, except as by the appended claims.

What is claimed:

1. An EMI feedthrough filter terminal assembly, comprising:
   a feedthrough filter capacitor including first and second sets of electrode plates, a passageway therethrough having a first termination surface conductively coupling the first set of electrode plates, and a second termination surface exteriorly coupling the second set of electrode plates;
   a conductive ferrule adjacent to the feedthrough filter capacitor; at least one conductive terminal pin extending through the passageway in conductive relation with the first set of electrode plates, and through the ferrule in non-conductive relation;
   an insulator fixed to the ferrule for conductively isolating the terminal pin from the ferrule; and
   an oxide resistant conductive hermetic seal between the insulator and the ferrule, the oxide resistant conductive seal including an oxide resistant conductive pad on a surface of the ferrule conductively coupled to the second termination surface.

2. The terminal assembly of claim 1, including a conductive connector extending between the second termination surface and the oxide resistant conductive pad.

3. The terminal assembly of claim 2, wherein the conductive connector is taken from the group consisting of conductive polyimide, solder, weld or braze.

4. The terminal assembly of claim 1, wherein the oxide resistant conductive pad comprises a noble metal.

5. The terminal assembly of claim 4, wherein the noble metal is taken from the group consisting of gold, platinum, and oxide resistant alloys thereof.

6. The terminal assembly of claim 1, wherein the second termination surface comprises a plurality of second termination surfaces and wherein the oxide resistant conductive pad includes a corresponding plurality of pads conductively coupled to the plurality of second termination surfaces.

7. The terminal assembly of claim 1, including means for hermetically sealing passage of the terminal pin through the ferrule.

8. The terminal assembly of claim 1, wherein the ferrule and the insulator comprise a pre-fabricated hermetic terminal pin sub-assembly.

9. The terminal assembly of claim 1, wherein the first passageway through the feedthrough filter capacitor comprises a plurality of first passageways each having a distinct first termination surface conductively coupled to a distinct first set of electrode plates, and wherein the at least one conductive terminal pin comprises a terminal pin extending through each of the plurality of first passageways.

10. The terminal assembly of claim 1, including an insulative washer disposed between the feedthrough filter capacitor and the insulator.

11. The terminal assembly of claim 10, wherein the insulative washer comprises a thermal plastic polyimide supported tape.

12. The terminal assembly of claim 11, wherein the thermal plastic polyimide supported tape comprises Ableloc.

13. The terminal assembly of claim 10, wherein the washer includes a gap adjacent to the terminal pin.

14. The terminal assembly of claim 1, including a second oxide resistant conductive pad conductively attached to the at least one terminal pin, and means for conductively coupling the second oxide resistant conductive pad to the first termination surface independently of the terminal pin.

15. The terminal assembly of claim 14, wherein the second oxide resistant conductive pad comprises a noble metal.

16. The terminal assembly of claim 1, specifically constructed for medical implant applications.

17. The terminal assembly of claim 16, wherein the medical implant applications include cardiac pacemakers, implantable cardioverter defibrillators, cochlear implants, neuro-stimulators, internal drug pumps, bone growth stimulators, artificial organs, artificial hearts, hearing assist stimulators, artificial limbs, artificial eyes, muscle actuators, and deep brain stimulators for seizure control, pain management and gene therapy.

18. The terminal assembly of claim 1, wherein the oxide resistant conductive pad is applied through a soldering process.

19. The terminal assembly of claim 1, wherein the oxide resistant conductive pad is applied through a physical vapor deposition process.

20. The terminal assembly of claim 1, wherein the oxide resistant conductive pad is applied through an electroplating process.

21. The terminal assembly of claim 1, wherein the oxide resistant conductive pad is applied through a plasma arc deposition process.

22. The terminal assembly of claim 1, wherein the oxide resistant conductive pad is applied through an ion beam process.

23. The terminal assembly of claim 1, wherein the oxide resistant conductive pad is applied through a chemical vapor deposition process.

24. The terminal assembly of claim 1, wherein the oxide resistant conductive pad is applied through a laser ablation process.

25. The terminal assembly of claim 1, wherein the oxide resistant conductive pad comprises a gold braze.

26. The terminal assembly of claim 25, wherein the oxide resistant conductive pad is attached, at least in part, to a titanium/molybdenum surface.

27. The terminal assembly of claim 1, wherein the terminal pin comprises an integral oxide resistant biostable wire bond pad on a body fluid side of the terminal assembly.

28. The terminal assembly of claim 27, wherein the wire bond pad comprises a noble metal.

29. The terminal assembly of claim 28, wherein the noble metal is taken from the group consisting of gold, platinum, and oxide resistant alloys thereof.

30. The terminal assembly of claim 27, including a mating wire bond cap attached to the terminal pin opposite the wire bond pad.

31. The terminal assembly of claim 30, wherein the wire bond cap comprises a material taken from the group consisting of tantalum, molybdenum, titanium, rhodium, titanium alloys, osmium, silver and silver alloys, vanadium, platinum, niobium, platinum alloys, stainless steel, tungsten, rhenium, zirconium, vanadium and ruthenium.

32. An EMI feedthrough filter terminal assembly, comprising:
a feedthrough filter capacitor including first and second sets of electrode plates, a passageway therethrough having a first termination surface conductively coupling the first set of electrode plates, and a plurality of second termination surfaces exteriorly coupling the second set of electrode plates;
a conductive ferrule adjacent to the feedthrough filter capacitor;
at least one conductive terminal pin extending through the passageway in conductive relation with the first set of electrode plates, and through the ferrule in non-conductive relation;
an insulator fixed to the ferrule for conductively isolating the terminal pin from the ferrule;
an oxide resistant hermetic seal between the insulator and the ferrule, the hermetic seal including a plurality of conductive pads of oxide resistant biostable material, on a surface of the ferrule conductively coupled to the plurality of second termination surfaces; and
conductive connectors extending between the respective second termination surfaces and the conductive pads.

33. The terminal assembly of claim 32, including means for hermetically sealing passage of the terminal pin through the ferrule.

34. The terminal assembly of claim 32, wherein the ferrule and the insulator comprise a pre-fabricated hermetic terminal pin sub-assembly.

35. The terminal assembly of claim 32, wherein the first passageway through the feedthrough filter capacitor comprises a plurality of first passageways each having a distinct first termination surface conductively coupled to a distinct first set of electrode plates, and wherein the at least one conductive terminal pin comprises a terminal pin extending through each of the plurality of first passageways.

36. The terminal assembly of claim 32, including an insulative washer disposed between the feedthrough filter capacitor and the insulator.

37. The terminal assembly of claim 36, wherein the insulative washer comprises a thermal plastic polyimide supported tape.

38. The terminal assembly of claim 37, wherein the thermal plastic polyimide supported tape comprises Ableloc.

39. The terminal assembly of claim 36, wherein the washer includes a gap adjacent to the terminal pin.

40. The terminal assembly of claim 32, including a second conductive pad of oxide resistant biostable material conductively attached to the at least one terminal pin, and means for conductively coupling the second pad to the first termination surface independently of the terminal pin.

41. The terminal assembly of claim 40, wherein the conductive pads comprise a noble metal.

42. The terminal assembly of claim 41, wherein the noble metal is taken from the group consisting of gold, platinum, and oxide resistant alloys thereof.

43. The terminal assembly of claim 40, wherein the conductive pads comprise a material taken from the group consisting of tantalum, molybdenum, titanium, rhodium, titanium alloys, osmium, silver and silver alloys, vanadium, platinum, niobium, platinum alloys, stainless steel, tungsten, rhenium, zirconium, vanadium and ruthenium.

44. The terminal assembly of claim 32, specifically constructed for medical implant applications.

45. The terminal assembly of claim 44, wherein the medical implant applications include cardiac pacemakers, implantable cardioverter defibrillators, cochlear implants, neuro-stimulators, internal drug pumps, bone growth stimulators, artificial organs, artificial hearts, hearing assist stimulators, artificial limbs, artificial eyes, muscle actuators, and deep brain stimulators for seizure control, pain management, and gene therapy.

46. The terminal assembly of claim 32, wherein the oxide resistant conductive pad comprises a gold braze.

47. The terminal assembly of claim 46, wherein the terminal pin comprises an integral oxide resistant biostable wire bond pad on a body fluid side of the terminal assembly.

48. The terminal assembly of claim 32, wherein the terminal pin comprises an integral oxide resistant biostable wire bond pad on a body fluid side of the terminal assembly.

49. The terminal assembly of 48, wherein the wire bond pad comprises a noble metal.

50. The terminal assembly of claim 49, wherein the noble metal is taken from the group consisting of gold, platinum, and oxide resistant alloys thereof.

51. The terminal assembly of claim 48, including a mating wire bond cap attached to the terminal pin opposite the wire bond pad.

52. The terminal assembly of claim 51, wherein the wire bond cap comprises a material taken from the group consisting of tantalum, molybdenum, titanium, rhodium, titanium alloys, osmium, silver and silver alloys, vanadium, platinum, niobium, platinum alloys, stainless steel, tungsten, rhenium, zirconium, vanadium and ruthenium.

53. An EMI feedthrough filter terminal assembly for use in medical implant applications, comprising:
- a feedthrough filter capacitor including first and second sets of electrode plates, a plurality of passageways therethrough each having a distinct first termination surface conductively coupled to a distinct first set of electrode plates, and a plurality of second termination surfaces exteriorly coupling the second set of electrode plates;
- a conductive ferrule adjacent to the feedthrough filter capacitor;
- a plurality of terminal pins corresponding with the number of passageways through the feedthrough filter capacitor, each terminal pin extending through a respective passageway in conductive relation with the corresponding distinct first set of electrode plates, and through the ferrule in non-conductive relation;
- an insulator fixed to the ferrule for conductively isolating the terminal pins from the ferrule, wherein the ferrule and the insulator comprise a pre-fabricated hermetic terminal pin sub-assembly;
- an oxide resistant hermetic seal between the insulator and the ferrule, the hermetic seal including a plurality of conductive pads of oxide resistant biostable material on a surface of the ferrule conductively coupled to the plurality of second termination surfaces; and
- conductive connectors extending between each of the respective second termination surfaces and conductive pads.

54. The terminal assembly of claim 53, including an insulative washer disposed between the feedthrough filter capacitor and the insulator.

55. The terminal assembly of claim 54, wherein the insulative washer comprises a thermal plastic polyimide supported tape.

56. The terminal assembly of claim 55, wherein the thermal plastic polyimide supported tape comprises Ableloc.

57. The terminal assembly of claim 53, including a second conductive pad of oxide resistant biostable material conductively attached to the at least one terminal pin, and means for conductively coupling the second conductive pad to the first termination surface independently of the terminal pin.

58. The terminal assembly of claim 57, wherein the conductive pads comprise a noble metal.

59. The terminal assembly of claim 58, wherein the noble metal is taken from the group consisting of gold, platinum, and oxide resistant alloys thereof.

60. The terminal assembly of claim 57, wherein the conductive pads comprise a material taken from the group consisting of tantalum, molybdenum, titanium, rhodium, titanium alloys, osmium, silver and silver alloys, vanadium, platinum, niobium, platinum alloys, stainless steel, tungsten, rhenium, zirconium, vanadium and ruthenium.

61. The terminal assembly of claim 53, including means for hermetically sealing passage of the terminal pin through the ferrule.

62. The terminal assembly of claim 53, wherein the medical implant applications include cardiac pacemakers, implantable cardioverter defibrillators, cochlear implants, neuro-stimulators, internal drug pumps, bone growth stimulators, artificial organs, artificial hearts, hearing assist stimulators, artificial limbs, artificial eyes, muscle actuators and deep brain stimulators for seizure control, pain management, and gene therapy.

63. The terminal assembly of claim 53, wherein the oxide resistant conductive pad comprises a gold braze attached, at least in part, to a titanium/molybdenum surface.

64. The terminal assembly of claim 53, wherein the oxide resistant conductive pad is applied through any one of the following: a soldering process, a physical vapor deposition process, an electroplating process, a plasma arc deposition process, an ion beam process, a chemical vapor deposition process, or a laser ablation process.

65. The terminal assembly of claim 53, wherein the terminal pins each comprise an integral oxide resistant biostable wire bond pad on a body fluid side of the terminal assembly.

66. The terminal assembly of claim 65, wherein the wire bond pad comprises a noble metal.

67. The terminal assembly of claim 66, wherein the noble metal is taken from the group consisting of gold, platinum, and oxide resistant alloys thereof.

68. The terminal assembly of claim 65, including a mating wire bond cap attached to each terminal pin opposite the wire bond pad.

69. The terminal assembly of claim 68, wherein the wire bond cap comprises a material taken from the group consisting of tantalum, molybdenum, titanium, rhodium, titanium alloys, osmium, silver and silver alloys, vanadium, platinum, niobium, platinum alloys, stainless steel, tungsten, rhenium, zirconium, vanadium and ruthenium.

* * * * *